United States Patent
Noda et al.

(10) Patent No.: US 7,897,240 B2
(45) Date of Patent: Mar. 1, 2011

(54) NONWOVEN FABRIC

(75) Inventors: Yuki Noda, Kagawa (JP); Hideyuki Ishikawa, Kagawa (JP); Satoshi Mizutani, Kagawa (JP); Koichiro Tani, Kagawa (JP); Akihiro Kimura, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 371 days.

(21) Appl. No.: 11/755,376

(22) Filed: May 30, 2007

(65) Prior Publication Data

US 2007/0298213 A1 Dec. 27, 2007

(30) Foreign Application Priority Data

Jun. 23, 2006 (JP) .................................. 2006-174505
Sep. 29, 2006 (JP) .................................. 2006-270110

(51) Int. Cl.
*B32B 3/10* (2006.01)

(52) U.S. Cl. .......... 428/131; 428/113; 428/137; 428/138; 428/167; 428/170; 428/171; 428/172; 428/212; 428/213; 428/218; 442/327; 442/366; 442/414

(58) Field of Classification Search .................. 428/131, 428/134
See application file for complete search history.

(56) References Cited

U.S. PATENT DOCUMENTS

| | | | |
|---|---|---|---|
| 3,485,706 A * | 12/1969 | Evans | 428/134 |
| 4,016,317 A * | 4/1977 | Kalwaites | 428/88 |
| 4,016,319 A | 4/1977 | Marshall | |
| 4,038,452 A | 7/1977 | Kobayashi et al. | |
| 4,190,695 A * | 2/1980 | Niederhauser | 442/2 |
| 4,379,799 A | 4/1983 | Holmes et al. | |
| 4,582,666 A | 4/1986 | Kenworthy et al. | |
| 4,612,226 A * | 9/1986 | Kennette et al. | 428/134 |
| 4,695,500 A * | 9/1987 | Dyer et al. | 428/134 |
| 4,735,842 A * | 4/1988 | Buyofsky et al. | 428/134 |
| 4,787,947 A * | 11/1988 | Mays | 156/160 |
| 4,835,042 A * | 5/1989 | Dohzono et al. | 428/218 |
| 4,840,829 A * | 6/1989 | Suzuki et al. | 428/131 |
| 5,607,414 A * | 3/1997 | Richards et al. | 604/378 |
| 5,613,962 A | 3/1997 | Kenmochi et al. | |

(Continued)

FOREIGN PATENT DOCUMENTS

CN 1294904 5/2001

(Continued)

OTHER PUBLICATIONS

International Search Report of PCT/JP2007/061601 issued Aug. 7, 2007.

(Continued)

*Primary Examiner* — David R Sample
*Assistant Examiner* — Jeff A Vonch
(74) *Attorney, Agent, or Firm* — Lowe, Hauptman, Ham & Berner, LLP

(57) ABSTRACT

A nonwoven fabric that is not easily damaged during use is provided. A fiber web supported by a predetermined supporting member from the lower face side is blown with fluid, mainly composed of gas, from the upper face side of the fiber web to move fibers that constitute the fiber web, thereby forming at least a plurality of open areas. The nonwoven fabric includes a plurality of open areas continuously formed along a predetermined direction with a predetermined interval and a plurality of joining portions, each of which are formed between the open areas adjacent to each other in a predetermined direction.

16 Claims, 16 Drawing Sheets

U.S. PATENT DOCUMENTS

| | | | |
|---|---|---|---|
| 5,618,610 A | | 4/1997 | Tomita et al. |
| 5,733,625 A | * | 3/1998 | Tsuchiya et al. ............... 428/113 |
| 5,897,547 A | | 4/1999 | Schmitz |
| 5,900,109 A | | 5/1999 | Sanders et al. |
| 6,039,555 A | | 3/2000 | Tsuji et al. |
| 6,096,016 A | * | 8/2000 | Tsuji et al. .................... 604/378 |
| 6,395,957 B1 | * | 5/2002 | Chen et al. .................... 604/381 |
| 6,451,718 B1 | * | 9/2002 | Yamada et al. ................ 442/149 |
| 6,582,798 B2 | * | 6/2003 | Thomas ......................... 428/132 |
| 6,586,076 B1 | | 7/2003 | Mizutani et al. |
| 6,610,173 B1 | | 8/2003 | Lindsay et al. |
| 6,641,902 B1 | * | 11/2003 | Kobayashi et al. ........... 428/220 |
| 6,855,424 B1 | * | 2/2005 | Fitts et al. ..................... 428/376 |
| 6,867,156 B1 | | 3/2005 | White et al. |
| 6,936,333 B2 | | 8/2005 | Shizuno et al. |
| 7,507,463 B2 | * | 3/2009 | Noda et al. .................... 428/167 |
| 7,553,535 B2 | * | 6/2009 | Noda et al. .................... 428/156 |
| 7,662,462 B2 | * | 2/2010 | Noda et al. .................... 428/167 |
| 2002/0010449 A1 | | 1/2002 | Mizutani |
| 2003/0198784 A1 | | 10/2003 | Mizutani et al. |
| 2003/0232558 A1 | | 12/2003 | Moody, III et al. |
| 2005/0177121 A1 | | 8/2005 | Mizutani et al. |
| 2008/0289157 A1 | | 11/2008 | Higashinaka et al. |

FOREIGN PATENT DOCUMENTS

| | | |
|---|---|---|
| DE | 4437165 A1 | 4/1996 |
| DE | 102005036759 A1 | 8/2006 |
| EP | 0903136 A2 | 3/1999 |
| EP | 0926287 A1 | 6/1999 |
| EP | 1201213 A2 | 5/2002 |
| JP | 02-169718 A | 6/1990 |
| JP | 2-229255 A | 9/1990 |
| JP | 03137257 A | 6/1991 |
| JP | 6-330443 A | 11/1994 |
| JP | 08-060509 A | 3/1996 |
| JP | 08-216310 A | 8/1996 |
| JP | 2002-030557 A | 1/2002 |
| JP | 2002-136547 A | 5/2002 |
| JP | 2002-249965 A | 9/2002 |
| JP | 2003126147 | 5/2003 |
| JP | 2004-141640 A | 5/2004 |
| JP | 3587831 | 8/2004 |
| WO | 2005122817 A1 | 12/2005 |

OTHER PUBLICATIONS

International Search Report of PCT/JP2007/060543 issued Jul. 10, 2007.

International Search Report of PCT/JP2007/061445 issued Jul. 31, 2007.

International Search Report of PCT/JP2007/061444 issued Aug. 7, 2007.

Office Action issued Aug. 4, 2009, from U.S. Appl. No. 11/748,712, filed May 15, 2007.

European Search Report for Application No. EP07743982, mailed Apr. 8, 2010.

Office Action issued to U.S. Appl. No. 11/762,421, mailed Oct. 6, 2009.

Office Action issued to U.S. Appl. No. 11/748,712, mailed Mar. 23, 2010.

Office Action issued to CN Application No. 200780022784.6 mailed May 12, 2010.

Office Action issued to U.S. Appl. No. 11/762,421 mailed May 11, 2010.

Office Action issued to U.S. Appl. No. 11/748,186 mailed Jun. 22, 2010.

Office Action issued to U.S. Appl. No. 12/511,115, mailed Sep. 14, 2010.

* cited by examiner

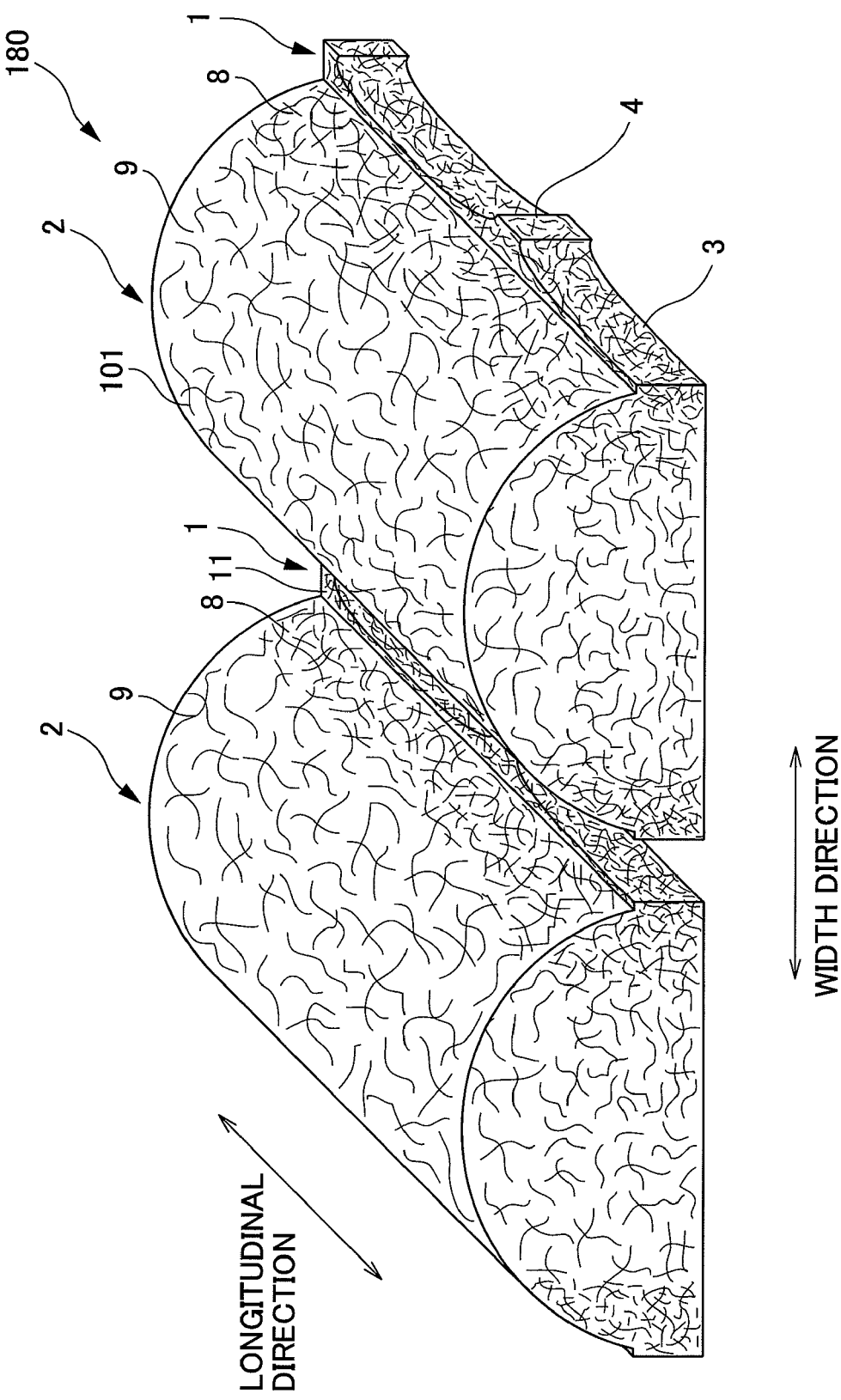

NONWOVEN FABRIC

This application is based on and claims the benefit of priority from Japanese Patent Application No. 2006-174505, filed on Jun. 23, 2006, and Japanese Patent Application No. 2006-270110, filed on Sep. 29, 2006, the content of which are incorporated herein by reference.

BACKGROUND OF THE INVENTION

1. Field of the Invention

The present invention relates to nonwoven fabric.

2. Related Art

Conventionally, nonwoven fabrics are used in a variety of fields, for example, sanitary products such as disposable diaper and sanitary napkin, cleaning products such as wipers and medical products such as masks. Such nonwoven fabrics are used in many different fields, but when actually used in products of each of those fields, it is necessary that the nonwoven fabric are manufactured with the properties and structures appropriate for their intended use.

Nonwoven fabric is manufactured by, for example, using a dry method or a wet method to form a fiber layer (fiber web) and then to bond fibers forming the fiber layer by a chemical bond method or a thermal bond method for example. Methods for bonding the fibers forming the fiber layer includes a method for applying a physical force where a plurality of needles are repeatedly inserted into the fiber layer and a method of applying a physical force where aqueous steam is jetted to the fiber layer.

However, these methods have only entangled the fibers to one another and do not adjust the orientation or arrangement of the fibers in the fiber layer, the shape of the fiber layer or the like. In other words, these methods only manufactured a simple sheet-like nonwoven fabric.

Nonwoven fabric that include openings has previously been suggested and a method has been disclosed in Japanese Unexamined Patent Publication No. Hei 6-330443 (hereinafter referred to as Patent Document 1) according to which, an opening is provided in a nonwoven fabric by sandwiching the nonwoven fabric between a stamp including a projection, such as a outwardly-protruding needle, and a supporting body receiving the projection so that the projection penetrates the nonwoven fabric to provide a three-dimensional opening for example.

When a nonwoven fabric including openings is used as a surface sheet of an absorbent article for highly viscous liquid for example, it is preferable to use a structure in which a joining section between a first open area and a second open area is reduced in size in order to increase both the diameter and ratio of the open area. However, in the case of the nonwoven fabric disclosed in Patent Document 1, a fiber assembly constituting the nonwoven fabric is pressed between the projection part and the receiving supporting body to cause concavities and convexities and openings. Thus, the joining section between the open areas has substantially the same density as that of the periphery of the open areas and the fiber orientation is mainly unchanged in the longitudinal direction. When the nonwoven fabric is used as a surface sheet in an absorbent article and the nonwoven fabric includes an arrangement of open areas among which small joining portions are provided, friction to the article in the width direction may cause fibers in the joining portion to easily unravel and result in damage to the article.

SUMMARY OF THE INVENTION

It is an objective of the present invention to provide a nonwoven fabric including open areas, nonwoven fabric being difficult to damage during use of the nonwoven fabric.

The present inventors have reached the present invention by finding that a gas can be blown to an upper face of a fiber web, supported by a predetermined air permeable supporting member from the lower face, to move fiber, constituting the fiber web, to form at least an open area, a concave portion and a convex portion.

According to a first aspect of the present invention, nonwoven fabric having a first direction and a second direction, including: a plurality of open areas arranged in a first direction; and a plurality of joining portions each of which is provided between a predetermined open area in the plurality of open areas and another open area adjacent to the predetermined open area in the first direction, wherein each of the joining portions includes fibers with a greater content orientated in the second direction compared to that orientated in the first direction, and each of the joining portions has a fiber density that is greater than those of a plurality of peripheral regions formed along a region including the plurality of open areas and the plurality of joining portions.

In a second aspect of the nonwoven fabric as described in the first aspect of the present invention, each of the joining portions has a ratio of a length in the second direction to a length in the first direction of no greater than 0.7.

In a third aspect of the nonwoven fabric as described in either the first or second aspects of the present invention, each of the open areas is structured so that fibers around periphery edge of each of the open areas are oriented along the periphery edge of each of the open areas.

In a fourth aspect of the nonwoven fabric as described in any one of the first to third aspects of the present invention, each of the open areas has a substantially circular shape or a substantially oval shape.

In a fifth aspect of the nonwoven fabric as described in any one of the first to fourth aspects of the present invention, each of the open areas has a ratio of a diameter in the first direction to a diameter in the second direction of no greater than 1.

In a sixth aspect of the nonwoven fabric as described in any one of the first to fifth aspects of the present invention, each of the open areas has a length in the second direction of 4 to 30 mm.

In a seventh embodiment of the nonwoven fabric as described in any one of the first to sixth aspects of the present invention, the region including the plurality of open areas and the plurality of joining portions is provided at a plurality of groove portions that are recessed on a first face of the nonwoven fabric in the thickness direction, and the nonwoven fabric further includes a plurality of convex portions that are adjacent to and along the plurality of groove portions and that protrude from the first face in the thickness direction.

In an eighth aspect of the nonwoven fabric as described in the seventh aspect of the present invention, each of the groove portions has a height in the thickness direction of the nonwoven fabric that is no greater than 90% of the height of each of the convex portions.

In a ninth aspect of the nonwoven fabric as described in either the seventh or eighth aspects of the present invention, a predetermined convex portion of the plurality of convex portions has a different height from an adjacent convex portion arranged to across a predetermined groove portion of the plurality of groove portions.

In a tenth aspect of the nonwoven fabric as described in any one of the seventh to ninth aspects of the present invention, each of the convex portion has an apex portion having a substantially flat shape.

In an eleventh aspect of the nonwoven fabric as described in any one of the seventh to tenth aspects of the present invention, a second face of the nonwoven fabric opposite to the first face includes a plurality of protruding regions protruding in an opposite direction to a direction along which the convex portions protrude.

In a twelfth aspect of the nonwoven fabric as described in any one of the seventh to eleventh aspects of the present invention, the nonwoven fabric is undulating in the first direction.

In a thirteenth aspect of the nonwoven fabric as described in any one of the first to tenth aspects of the present invention, the second face of the nonwoven fabric is substantially flat.

In a fourteenth aspect of the nonwoven fabric as described in any one of the seventh to thirteenth aspects of the present invention, side sections of the plurality of convex portions include a higher content of fiber orientated in the first direction compared to that orientated in the second direction.

In a fifteenth aspect of the nonwoven fabric as described in any one of the seventh to fourteenth aspects of the present invention, each of the convex portions is structured so that a percent open area measured from the first face is greater than the percent open area measured from the second face of the nonwoven fabric.

In a sixteenth aspect of the nonwoven fabric as described in any one of the first to fifteenth aspects of the present invention, each of the joining portions has a fiber density of no less than 0.05 g/cm$^3$.

In a seventeenth aspect of the nonwoven fabric as described in any one of the first to sixteenth aspects of the present invention, fibers constituting the nonwoven fabric include water-repellent fibers.

According to the present invention, such nonwoven fabric can be provided with open areas that improve resistance to damage during use.

BRIEF DESCRIPTION OF THE DRAWINGS

FIG. 2 shows an expanded perspective view illustrating a region X as defined in FIG. 1;

FIG. 3A shows a plan view illustrating a mesh supporting member in which elongated members are arranged in parallel with an equal interval there between;

FIG. 3B shows a perspective view illustrating a mesh supporting member in which elongated members are arranged in parallel with an equal interval there between;

DETAILED DESCRIPTION OF THE INVENTION

Preferred embodiments of the present invention will now be explained with reference to the drawings.

Figure 1A:
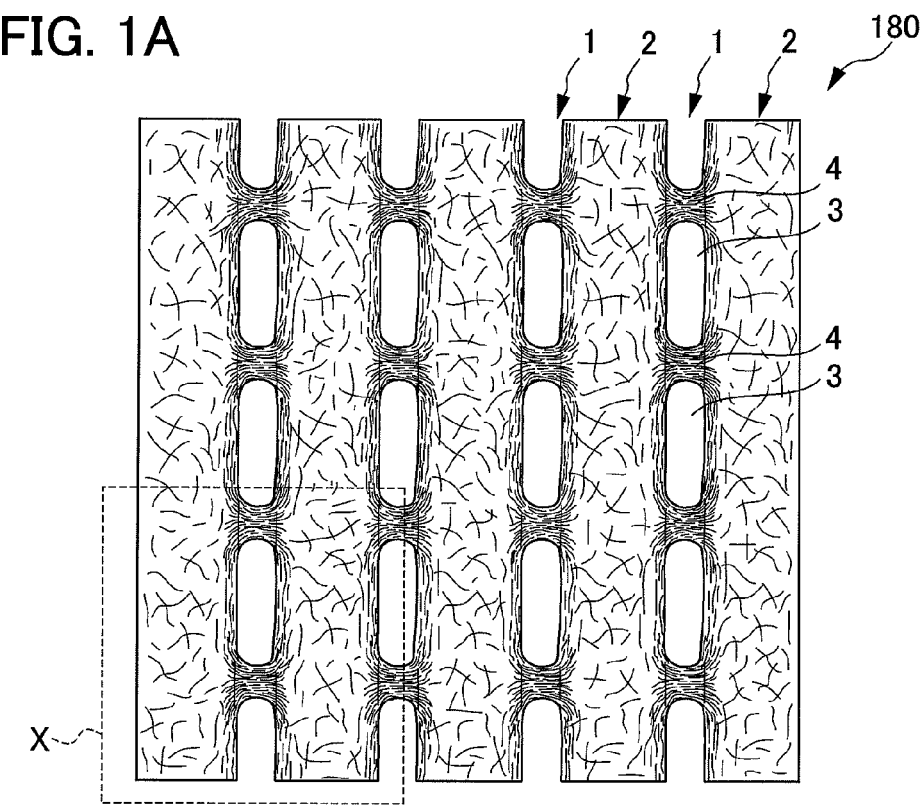
FIG. 1A shows a plan view of nonwoven fabric of the first embodiment.
Figure 1B:
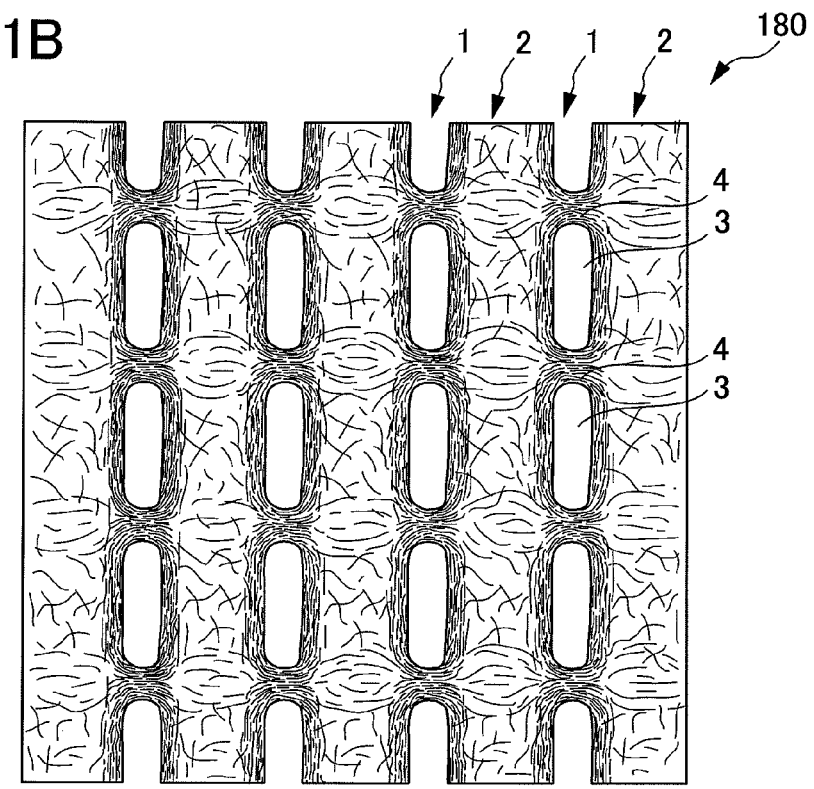
FIG. 1B shows a bottom view of the nonwoven fabric of the first embodiment.
Figure 3A:
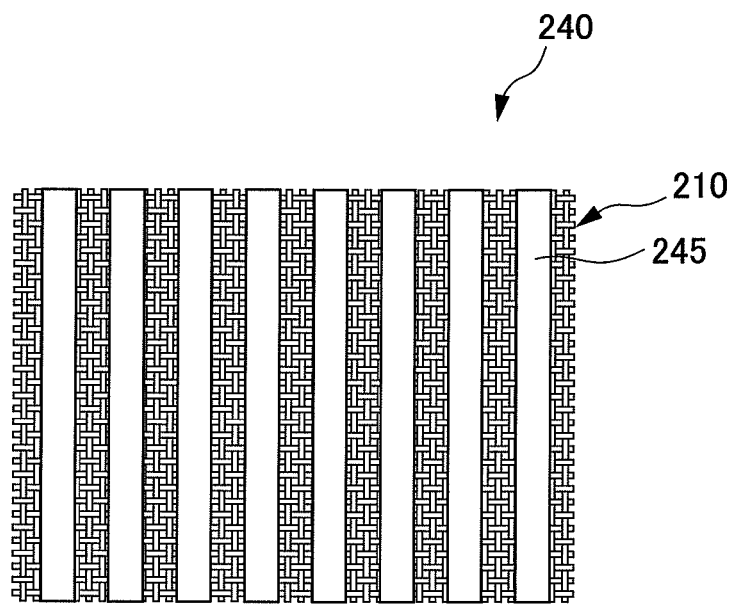
Figure 3B:
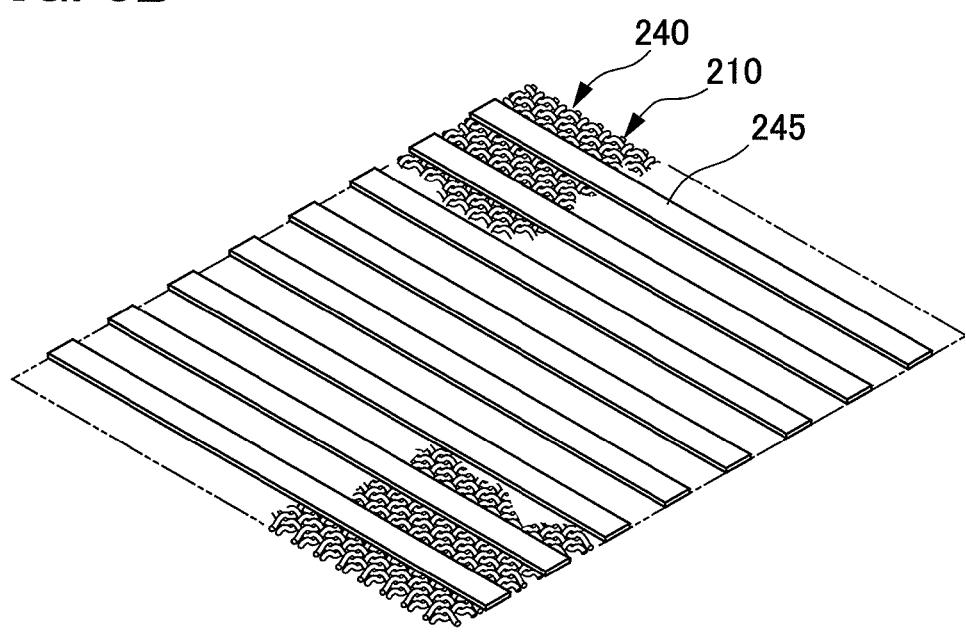
Figure 4:
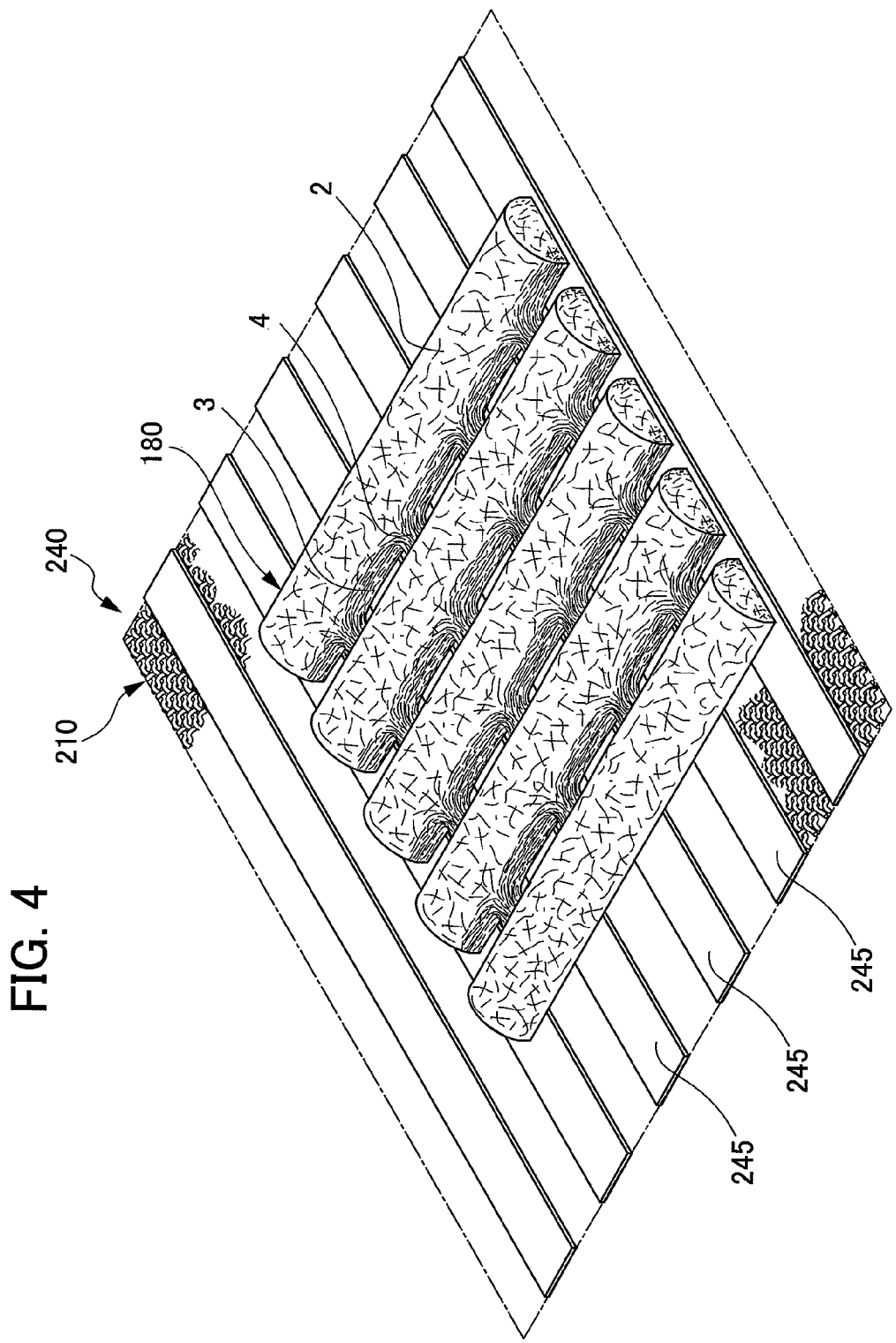
FIG. 4 shows an illustration of the nonwoven fabric of the first embodiment as described in FIG. 1 obtained by blowing gas to the upper face of the fiber web while the lower face is being supported by the supporting member as described in FIG. 3.
Figure 5:
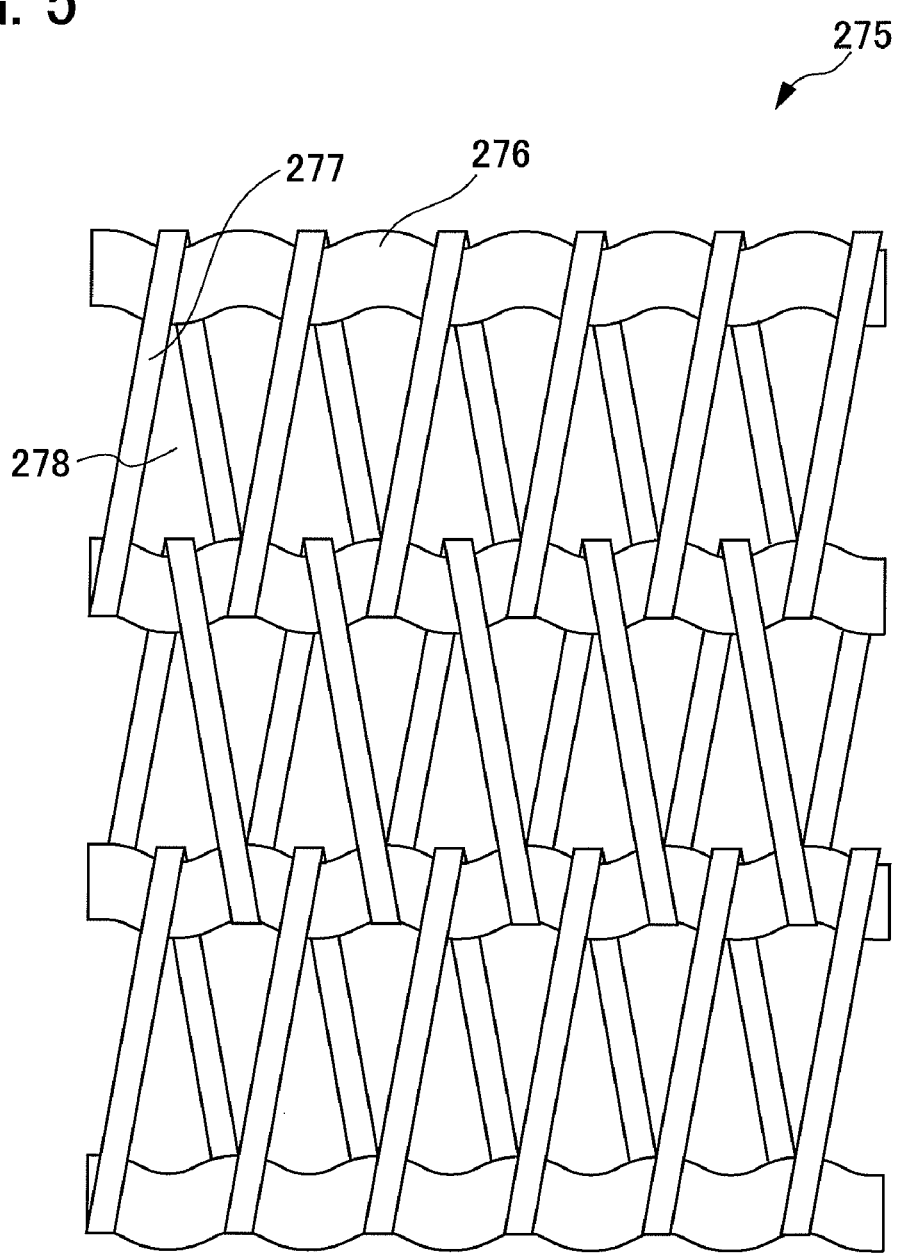
FIG. 5 shows an expanded front view illustrating another supporting member by which the nonwoven fabric of the first embodiment can be manufactured.
Figure 6:
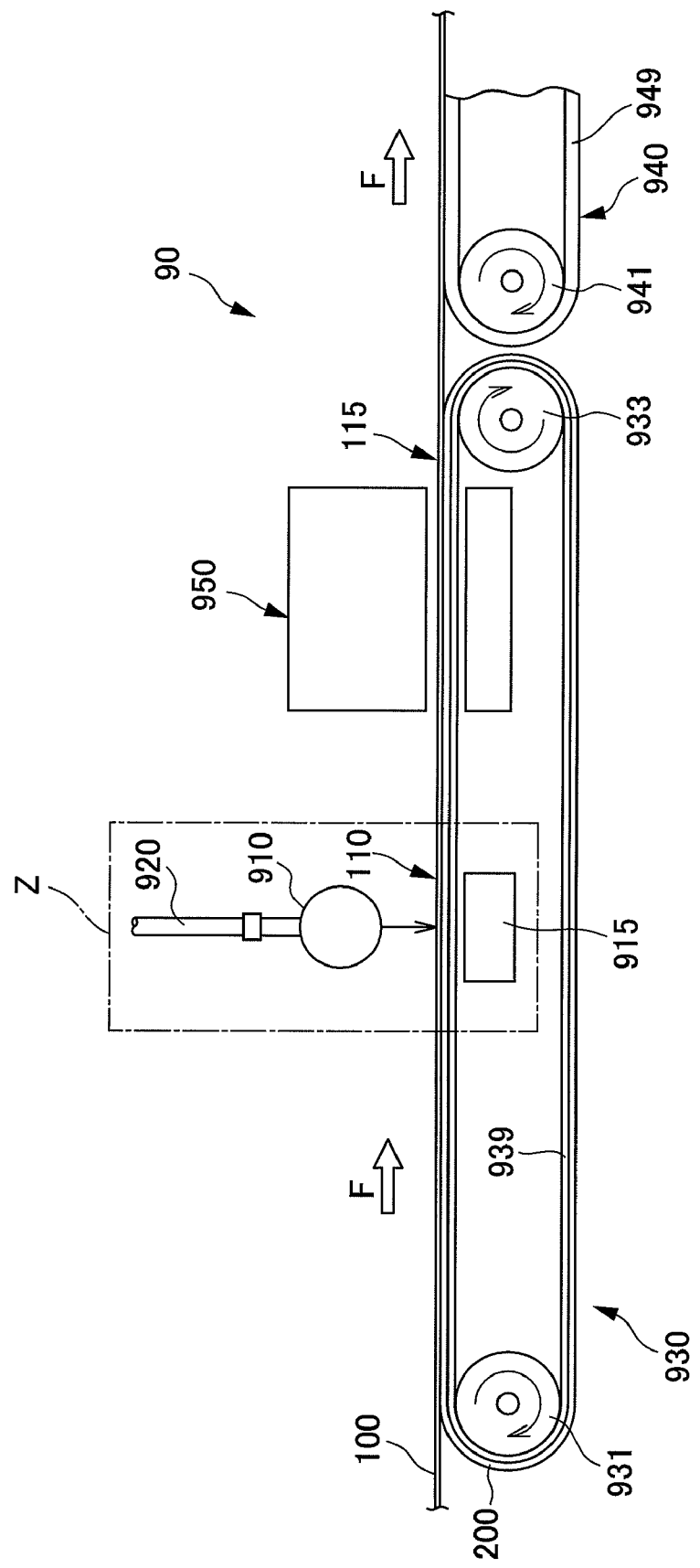
FIG. 6 shows a side view illustrating an apparatus for manufacturing the nonwoven fabric of the first embodiment.
Figure 7:
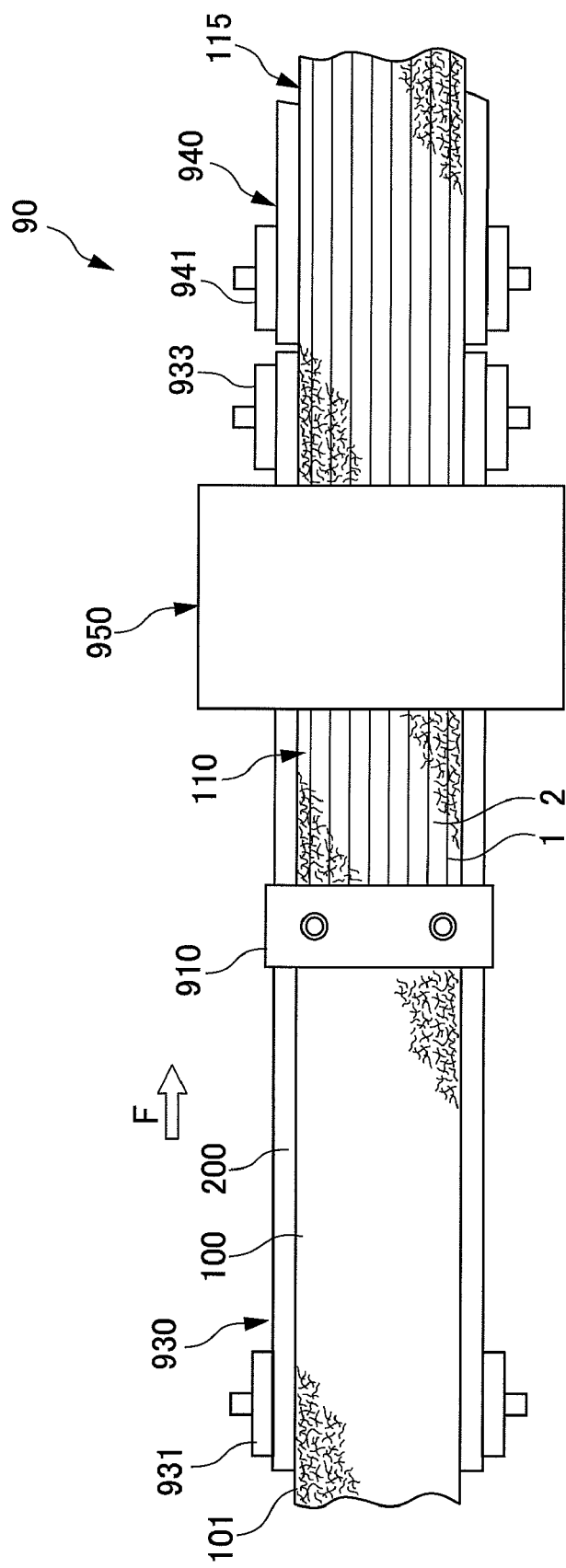
FIG. 7 shows a plan view illustrating the apparatus for manufacturing the nonwoven fabric as described in FIG. 6.
Figure 8:
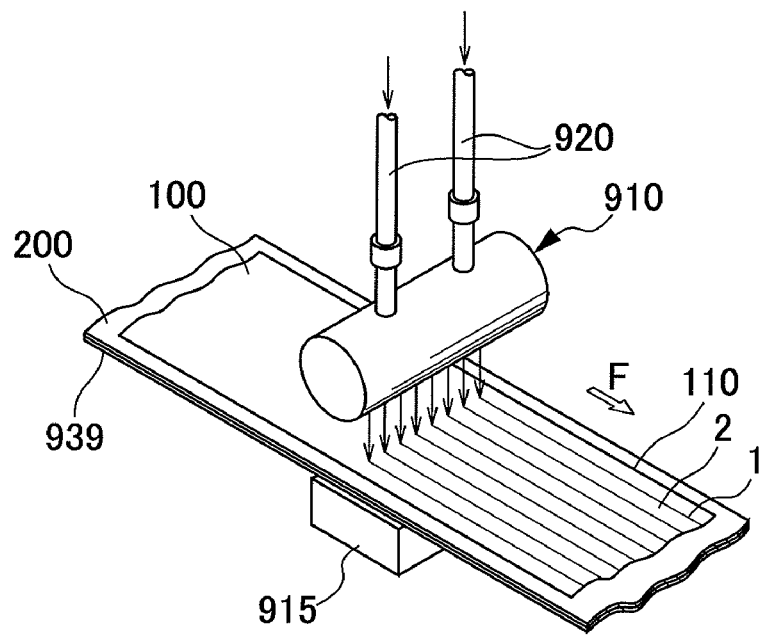
FIG. 8 shows an expanded perspective view illustrating a region Z as described in FIG. 6.
Figure 9:
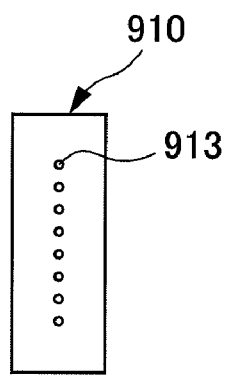
FIG. 9 shows a bottom view illustrating a blowing section as described in FIG. 8.

FIGS. 1A and 1B shows a plan view and a bottom view illustrating nonwoven fabric of the first embodiment. FIG. 2 shows an expanded perspective view illustrating a region X as defined in FIG. 1. FIGS. 3A and 3B show a plan view and a perspective view illustrating a mesh supporting member in which elongated members are arranged in parallel with an equal interval therebetween. FIG. 4 shows an illustration of the nonwoven fabric of the first embodiment as described in FIG. 1 obtained by blowing gas to the upper face of fiber web while the lower face is being supported by the supporting member described in FIG. 3. FIG. 5 shows an expanded front view illustrating another supporting member by which the nonwoven fabric of the first embodiment can be manufactured. FIG. 6 shows a side view illustrating an apparatus for manufacturing the nonwoven fabric of the first embodiment. FIG. 7 shows a plan view illustrating the nonwoven fabric manufacture apparatus described in FIG. 6. FIG. 8 shows an expanded perspective view illustrating a region Z as defined in FIG. 6. FIG. 9 shows a bottom view illustrating a blowing section as described in FIG. 8.

Figure 10:
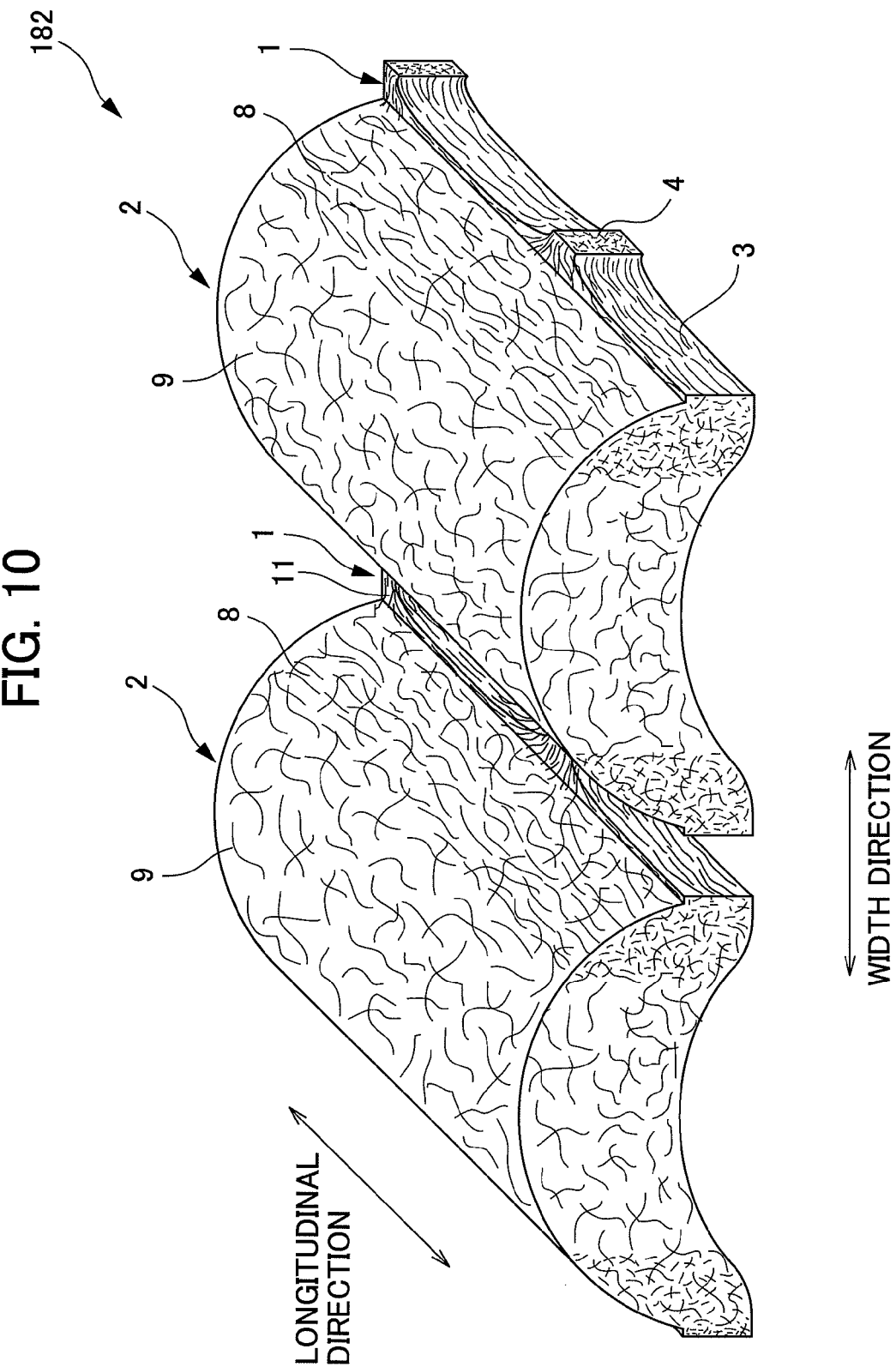
FIG. 10 shows a perspective cross sectional view illustrating a nonwoven fabric of the second embodiment.
Figure 11:
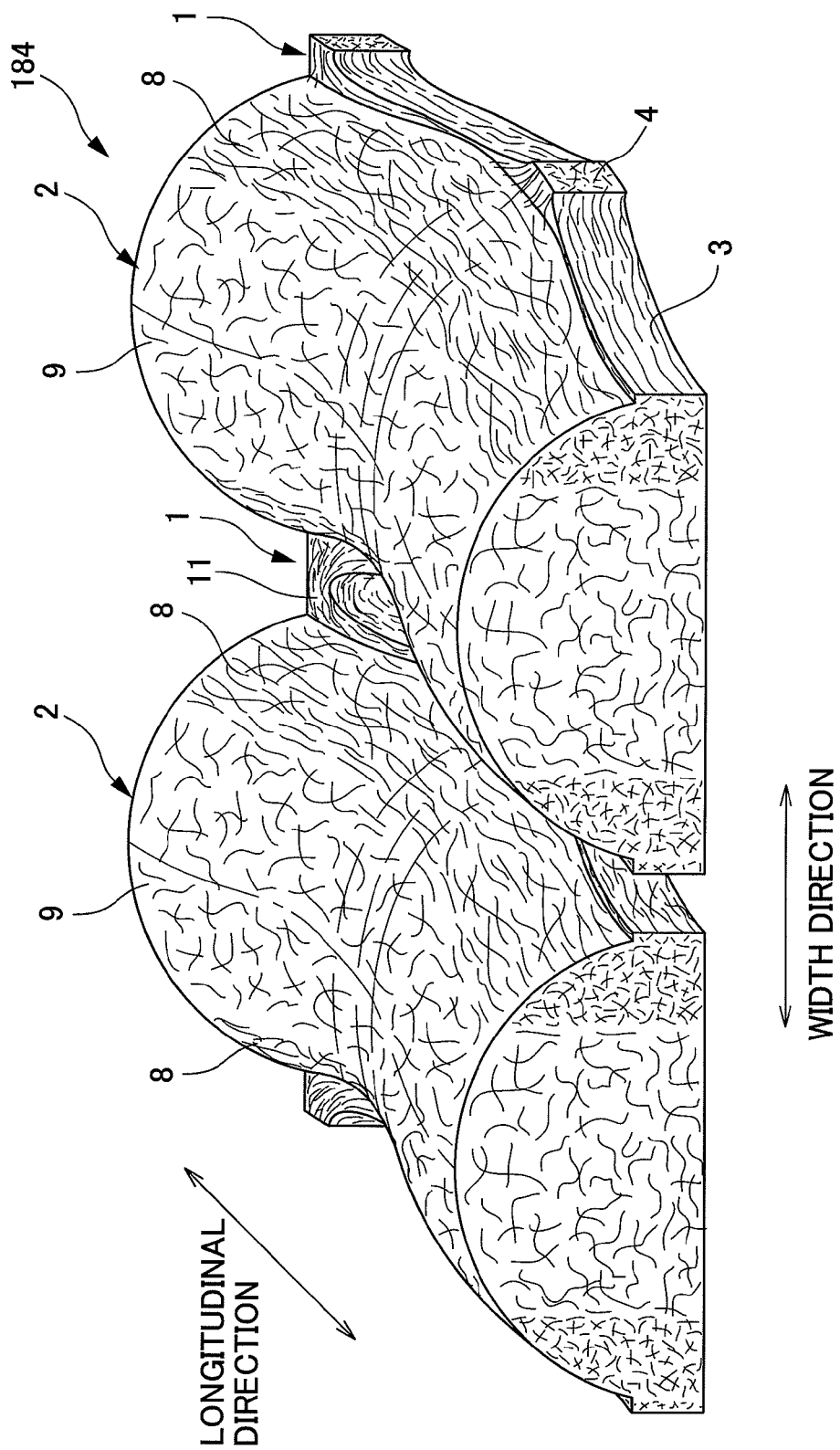
FIG. 11 shows a perspective cross sectional view illustrating a nonwoven fabric of the third embodiment.
Figure 12:
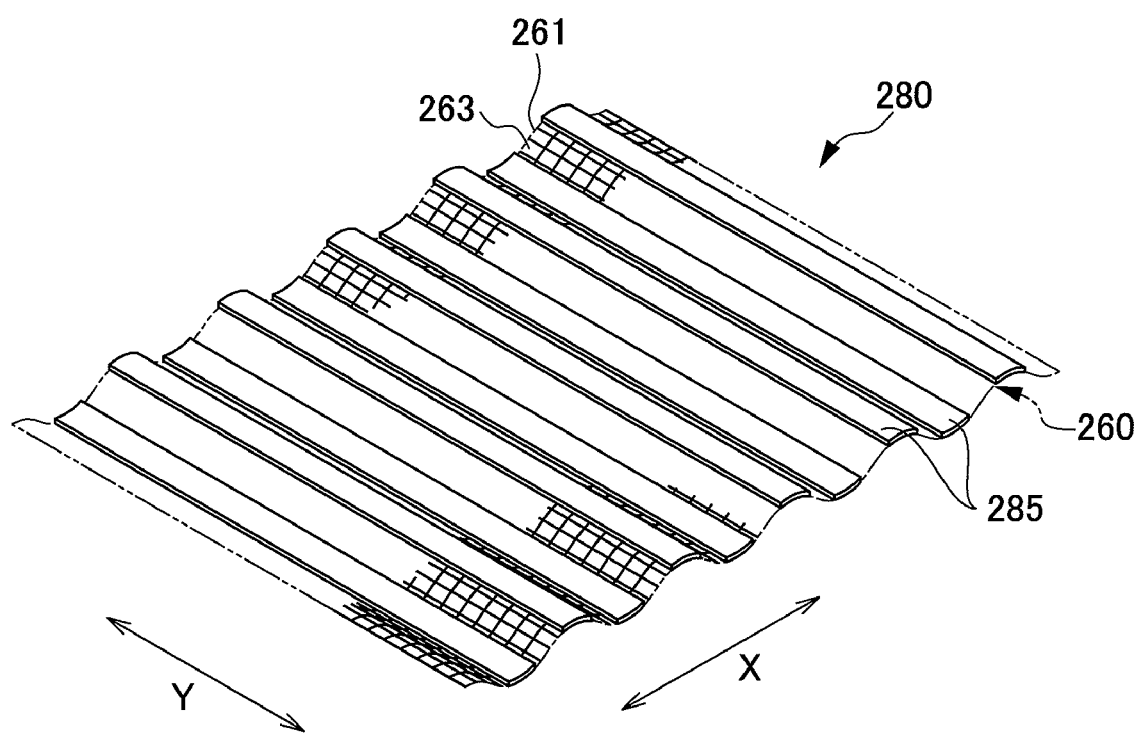
FIG. 12 shows an expanded perspective view illustrating a supporting member of the third embodiment.
Figure 13:
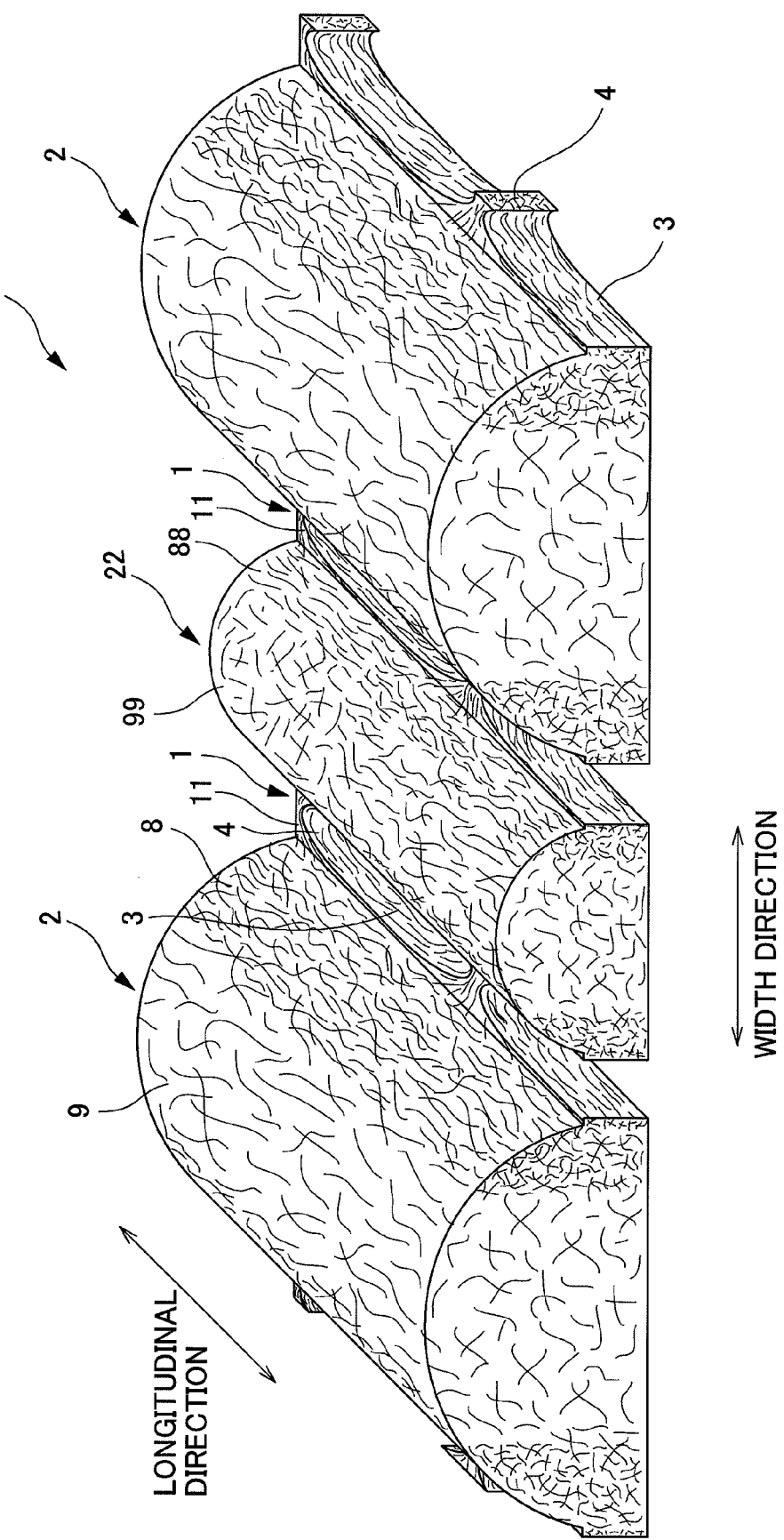
FIG. 13 shows a perspective cross sectional view illustrating a nonwoven fabric of the fourth embodiment.
Figure 14:
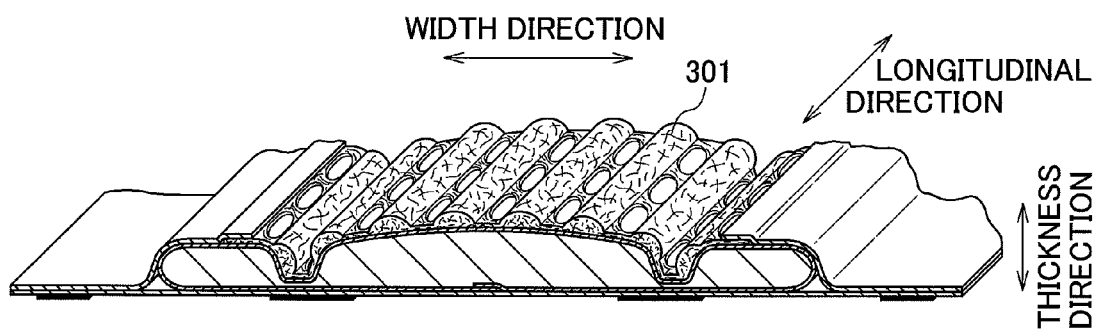
FIG. 14 shows a perspective view illustrating a nonwoven fabric according to the present invention when used as a surface sheet of a sanitary napkin.

FIG. 10 shows a perspective cross sectional view illustrating a nonwoven fabric of the second embodiment. FIG. 11 shows a perspective cross sectional view illustrating a nonwoven fabric of the third embodiment. FIG. 12 shows an expanded perspective view illustrating a supporting member of the third embodiment. FIG. 13 shows an expanded perspective view illustrating a nonwoven fabric of the fourth embodiment. FIG. 14 shows a perspective view illustrating the nonwoven fabric of the present invention when used as a surface sheet of a sanitary napkin.

Figure 15:
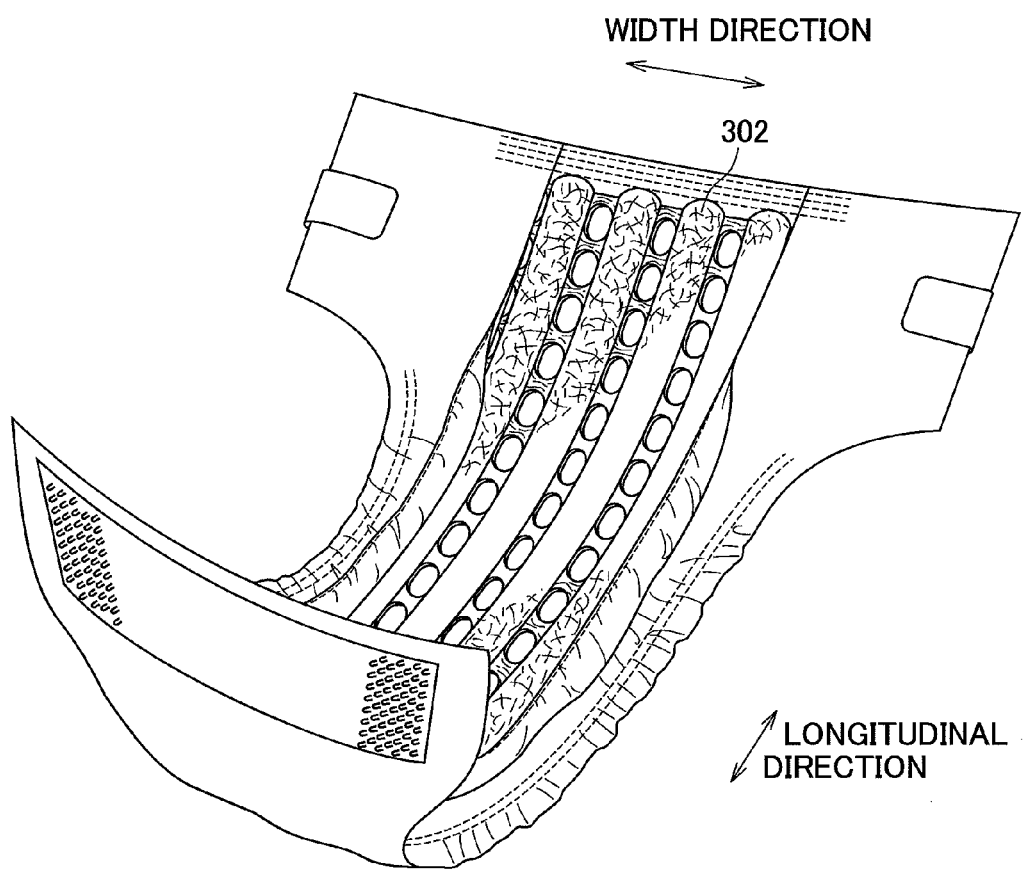
FIG. 15 shows a perspective view illustrating the nonwoven fabric of the present invention when used as a surface sheet of a diaper.
Figure 16:
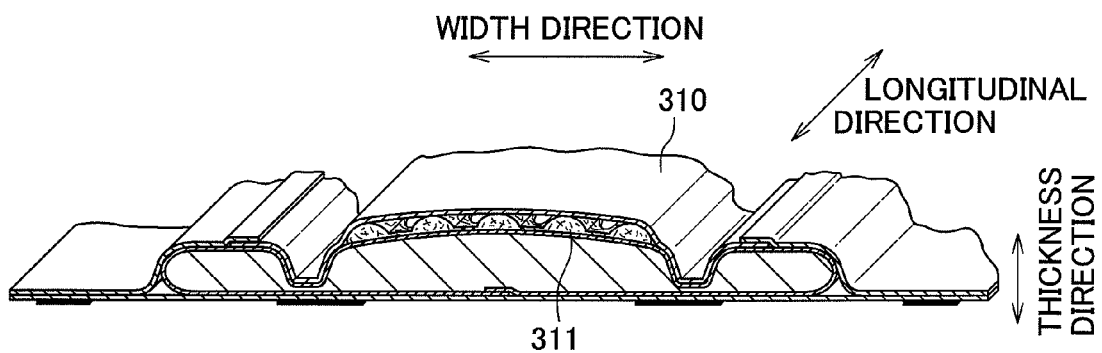
FIG. 16 shows a perspective view illustrating the nonwoven fabric of the present invention when used as an intermediate sheet of an absorbent article.
Figure 17:
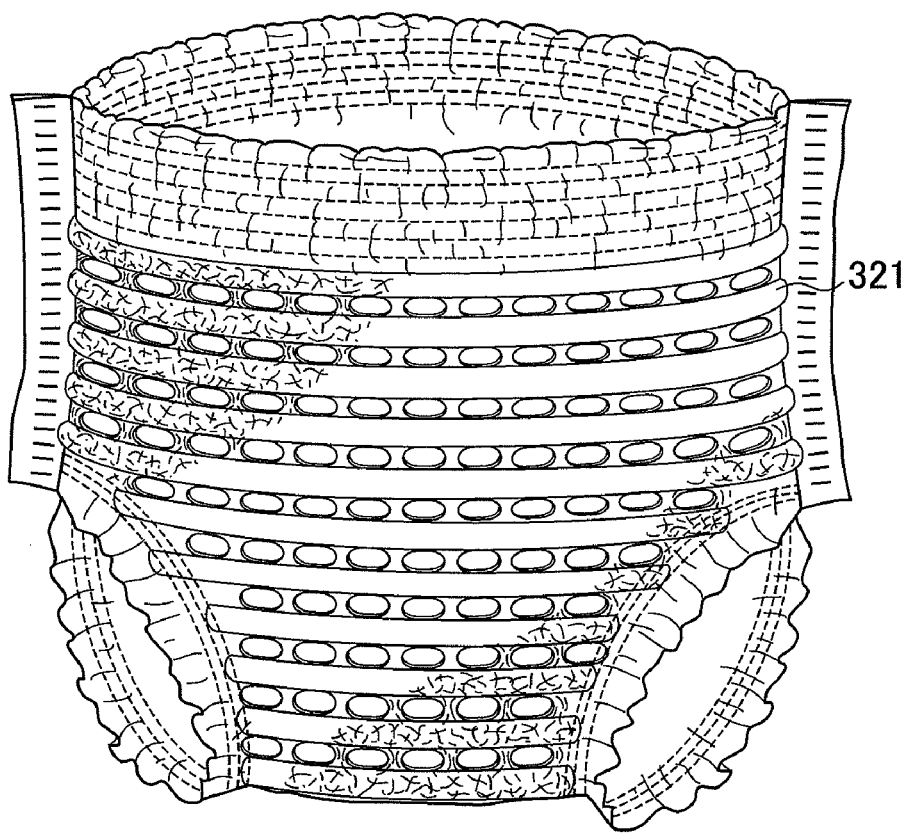
FIG. 17 shows a perspective view illustrating the nonwoven fabric of the present invention when used as an outermost of an absorbent article.

FIG. 15 shows a perspective view illustrating the nonwoven fabric of the present invention when used as a surface sheet of a diaper. FIG. 16 shows a perspective view illustrating the nonwoven fabric of the present invention when used as an intermediate sheet of an absorbent article. FIG. 17 shows a perspective view illustrating the nonwoven fabric of the present invention when used as an outermost of an absorbent article.

The nonwoven fabric of the present invention is obtained in the manner as described below. Specifically, fluid mainly composed of gas is blown to a fiber assembly that is supported by a predetermined air permeable supporting member from one surface side, that is shaped to have a substantially sheet-like shape, and that is composed of fibers having a sufficient degree of freedom to form at least a predetermined open area in the nonwoven fabric.

1. Embodiment 1

With reference to FIG. 1A, FIG. 1B, FIG. 2, and FIG. 4, the first embodiment of the nonwoven fabric of the present invention will be described.

1.1. Shape

As shown in FIG. 1A, FIG. 1B, and FIG. 2, nonwoven fabric 180 of the first embodiment is structured so that a plurality of groove portions 1 are arranged at one surface of the nonwoven fabric 180 along the first direction (hereinafter referred to as longitudinal direction) with a substantially equal interval therebetween. In the groove portions 1 of the nonwoven fabric, open areas 3 and joining portions 4 are alternately arranged with a substantially equal interval. The respective plurality of open area 3 is formed to have a substantially circular or a substantially elliptical shape. In the first embodiment, the groove portions 1 are arranged in parallel to one another with a substantially equal interval. However, the invention is not limited to this. The respective adjacent groove portions 1 also may be arranged with a different interval. Alternatively, intervals among the groove portions 1 also may be arranged in a varied manner.

Among the plurality of groove portions 1 arranged with a substantially equal interval therebetween, a plurality of convex portions 2 are arranged, respectively. These convex portions 2 are arranged in parallel to one another with a substantially equal interval therebetween as in the groove portions 1. In the first embodiment, the convex portions 2 of the nonwoven fabric 180 (thickness direction) have substantially the same height. However, adjacent convex portions 2 also may have different heights. For example, the heights of the convex portions 2 can be adjusted by adjusting an interval among blowing openings 913 (which will be described later) through which fluid, mainly composed of gas is blown. For example, the heights of the convex portions 2 can be reduced by reducing the intervals among the blowing openings 913 or the heights of the convex portions 2 can be increased by increasing the intervals among the blowing openings 913. Alternatively, the convex portions 2 having two different heights can be alternately provided by providing a narrow interval and a wide interval among the convex portions 2. By partially reducing the height of the convex portion 2, the area in contact with skin can be reduced.

The convex portion 2 of the nonwoven fabric 180 has a height in the thickness direction that is greater than the height of the groove portion 1. The convex portion 2 of the nonwoven fabric 180 exemplarily can have a height in the thickness direction of 0.3 to 15 mm or preferably 0.5 to 5 mm. The convex portion 2 can exemplarily have a length in a width direction of 0.5 to 30 mm or preferably 1.0 to 10 mm. Adjacent convex portions 2 across the groove portion 1 can exemplarily have a distance therebetween 0.5 to 30 mm or preferably 3 to 10 mm.

The groove portion 1 of the nonwoven fabric 180 has a height in the thickness direction that is less than that of the convex portion 2. Specifically, the groove portion 1 of the nonwoven fabric 180 can exemplarily have a height in the thickness direction of no greater than 90%, preferably 1 to 50%, or more preferably 0 to 20% of the height of the convex portion 2 in the thickness direction. The length of the groove portion 1 in the width direction can be, for example, of 0.1 to 30 mm or preferably 0.5 to 10 mm. Adjacent groove portions 1 sandwiching the convex portion 2 can exemplarily have a distance therebetween of 0.5 to 20 mm or preferably 3 to 10 mm. A height of 0% in the thickness direction means that the region is the open area 3.

According to the above described design, when the nonwoven fabric 180 is used as a surface sheet of an absorbent article for example, the groove portion 1 can suppress a large amount of predetermined liquid discharged to the nonwoven fabric 180 from spreading over a wide area. Even when an excessive external pressure is applied to the article to crush the convex portions 2, spaces provided by the groove portions 1 can be more easily be maintained to suppress, even when predetermined liquid is discharged to the nonwoven fabric 180 while the article receiving an external pressure, the liquid from spreading over a wide area of the surface. Furthermore, even when predetermined liquid once absorbed by absorbent material or the like returns to the surface of the nonwoven fabric 180 under an external pressure, the concavities and convexities provided in the surface of the nonwoven fabric 180 may provide a smaller contact area with skin thus reducing the likelihood of liquid being attached to a skin.

The height, pitch, or width of the groove portion 1 or the convex portion 2 is measured in the manner as described below. For example, the nonwoven fabric 180, in the absence of external pressure, is placed on a table to measure the height, pitch, or width of the groove portion 1 based on a photograph or image of the cross section of the nonwoven fabric 180 taken by a microscope.

The height (length in the thickness direction) of the nonwoven fabric 180 is measured by measuring a length from the lowest position (i.e., table surface) of the nonwoven fabric 180 to the highest positions of the convex portion 2 and the groove portion 1, respectively.

The pitch between the convex portions 2 is measured by measuring the distance between the centers of adjacent convex portions 2. The pitch between the groove portions 1 is similarly measured by measuring the distance between the centers of adjacent groove portions 1.

The width of the convex portion 2 is measured by measuring the maximum width of the bottom face of the convex portion 2 from the lowest position of the nonwoven fabric 180 (i.e., table surface) to an upper part. The width of the groove portion 1 is similarly measured.

The cross sectional shape of the convex portion 2 is not particularly limited. For example, the cross sectional shape of the convex portion 2 may be a dome-like shape, a trapezoidal shape, a triangular shape, a Ω-like shape, or a rectangular shape for example. In order to provide a soft touch to skin, a part in the vicinity of the top face and the side face of the convex portion 2 are preferably curved. In order to maintain the spaces provided by the groove portions 1 even when convex portions 2 are crushed by an external pressure, the convex portion 2 preferably has a width that is reduced from the bottom face to the top face. The convex portion 2 preferably has a top face curved to have a substantially dome-like shape (curved surface).

As shown in FIG. 1A and FIG. 1B, the nonwoven fabric 180 of the first embodiment is a nonwoven fabric in which a plurality of open areas 3 is formed along the groove portion 1. And joining portions 4 are formed between the respective plurality of open areas 3 for connecting the convex portions 2 adjacent to the groove portions 1. In other words, the plurality of joining portions 4 formed in a predetermined interval are joined the convex portions 2 adjacent to each other.

Although the first embodiment arranges the open areas 3 to have a substantially equal interval, the open areas 3 also may be arranged to have different intervals.

One open area 3 may exemplarily have a length in the longitudinal direction and a length in the width direction of 4 to 30 mm or preferably 5 to 10 mm.

A ratio of a length in the longitudinal direction to a length in the width direction of one open area 3 may exemplarily be no greater than 1.0.

The height of the nonwoven fabric 180 at the joining portion 4 in the thickness direction may exemplarily be equal to or less than the height of the convex portion 2 of the nonwoven fabric 180 in the thickness direction may be preferably 20 to 100%, or more preferably may be 40 to 70%.

A ratio of the length of one joining portion 4 in the longitudinal direction to the length in the width direction is preferably no greater than 0.7. When the ratio is no greater than 0.7, the joining portion 4 has a fiber density that is greater than that of the fiber density of the convex portion 2.

When the ratio is greater than 0.7, the joining portion 4 has a fiber density that is less than that of the fiber density of the convex portion 2.

The longitudinal direction of the joining portion 4 means a direction along which the groove portion 1 or the convex portion 2 extends. The width direction of the joining portion 4 means a direction that is substantially orthogonal to a direction along which the groove portion 1 or the convex portion 2 extends. In other words, the width direction of the joining portion 4 extends along a width of the groove portion 1 or a width of the open area 3. Thus, the length of the joining portion 4 in the width direction is the length of the width of the groove portion 1 or the length of the width of the open area 3.

Specifically, the length of the joining portion 4 in the width direction exemplarily may be 4 to 30 mm or preferably 5 to 10 mm.

The joining portion 4 has a substantially rectangular cross-sectional shape in the longitudinal direction of the nonwoven fabric. It is noted that the cross-sectional shape of the joining portion 4 in the longitudinal direction is not limited to the substantially rectangular one and may also be a dome-like shape, a trapezoidal shape, a triangular shape, a Ω-like shape or the like. However, in order to suppress predetermined liquid from dispersing at the groove portion 1, the cross-sectional shape of the joining portion 4 in the longitudinal direction is preferably a substantially rectangular one. The top face of the joining portion 4 is preferably a flat surface or a curved surface in order to prevent an external pressure causing the joining portion 4 to have a contact with skin for example to cause foreign-body sensation to the skin.

1.2. Fiber Orientation

As shown in FIG. 1A, FIG. 1B, or FIG. 2, the nonwoven fabric 180 is structured to include regions having different percent content of fibers orientated in the first direction (hereinafter also may be referred to as longitudinally orientated fibers) in which the fibers 101 are oriented along a region blown with fluid, mainly composed of gas, in the first direction (predetermined longitudinal direction in nonwoven fabric). The regions having different percent content can be exemplified as the convex portion 2 and the joining portion 4.

Fibers 101 oriented in the longitudinal direction are defined as fibers 101 that are oriented along the first direction within a range of −45 degrees to +45 degrees to a predetermined longitudinal direction as a direction (Machine Direction) along which nonwoven fabric or fiber web is sent via a machine for manufacturing nonwoven fabric. Fibers oriented in the first direction are called longitudinally orientated fibers. Fibers 101 oriented in the second direction (predetermined width direction in nonwoven fabric) are defined as those fibers 101 that are oriented along the second direction within a range of −45 degrees to +45 degrees to a predetermined width direction of the nonwoven fabric as a direction (Cross Direction) orthogonal to the Machine Direction. Fibers oriented in the width direction are called as laterally orientated fibers.

The convex portion 2 is preferably provided by appropriately mixing the longitudinally orientated fibers with the laterally orientated fibers. A part of the convex portion 2 at which the convex portion 2 has a contact with the open area 3 has a percent content of the longitudinally orientated fibers that is greater than that of the percent content of the laterally orientated fibers.

In a surface of the convex portion 2 opposed to the supporting member 240, a region adjacent to the joining portion 4 partially has a percent content of laterally orientated fibers that is greater than that of the percent content of laterally orientated fibers in other regions as shown in FIG. 1B and FIG. 2.

As described above, the groove portion 1 is a recessed region that is recessed by being directly subjected to fluid, mainly composed of gas (e.g., hot air), to be recessed in the thickness direction of the nonwoven fabric. The groove portion 1 also includes the open area 3 and the joining portion 4. By being blown with fluid, mainly composed of gas, the fibers 101 oriented in the longitudinal direction (longitudinally orientated fiber) are blown to a side section 8 of the convex portion 2. Then, more fibers 101 (laterally orientated fiber) oriented in the width direction are blown to the joining portion 4 by the blown fluid, mainly composed of gas, and/or fluid, mainly composed of gas, that is blown to an elongated member 245 as an impervious section of the supporting member 240 (which will be described later) to change the flow in a different direction. In other words, the fibers 10 at the periphery edge of the open area 3 are oriented along the open shape.

In the nonwoven fabric 180, the joining portion 4 has the least percent content of the longitudinally orientated fibers. In other words, the joining portion 4 has the greatest percent content of the laterally orientated fibers. Specifically, the joining portion 4 includes laterally orientated fibers with a percent content of 55 to 100% or preferably 60 to 100%. A percent content of laterally orientated fibers less than 55% causes difficulty in increasing the strength of nonwoven fabric in the width direction because the groove portion 1 has a low basis weight of web as will be described later. In this case, when the nonwoven fabric 180 is used as a surface sheet of an absorbent article for example, there is a risk in which friction between the article and a human body may cause the article to be twisted or broken during use.

Fiber orientation was measured by a digital microscope VHX-100 made by KEYENCE CORPORATION based on the following measurement method.

(1) Set a sample on an observation stand in an appropriate longitudinal direction.
(2) Focus a lens on fibers at the front side of the sample, excluding irregular protruding fibers.
(3) Set a photographing depth (depth) to create a 3D image of the sample on a PC screen.
(4) Then, convert the 3D image to a 2D image.
(5) Draw a plurality of parallel lines in a measurement range to equally divide the sample in the longitudinal direction.
(6) With regards to the respective cells subdivided by the parallel lines, whether the fiber orientation of the cells is in the first direction (longitudinal direction) or in the second direction (width direction) is observed to measure the number of fibers in the respective directions.

(7) Then, with regards to the total number of fibers in the set range, a ratio of the number of fibers oriented in the first direction (longitudinal direction) and a ratio of the number of fibers oriented in the second direction (width direction) are calculated.

1.3. Fiber Density Variation

As shown in FIG. 1A and FIG. 1B, the joining portion 4 has a greater higher fiber density than that of the convex portion 2.

Specifically, the joining portion 4 exemplarily has a fiber density of 0.05 g/cm$^3$ or more, preferably 0.10 to 0.50 g/cm$^3$, or more preferably 0.15 to 0.20 g/cm$^3$. When the joining portion 4 has a fiber density less than 0.05 g/cm$^3$, the joining portion 4 may be crushed when the convex portion 2 is crushed by an excessive external pressure.

The convex portion 2 has an average fiber density less than that of the joining portion 4. Specifically, the convex portion 2 exemplarily has an average fiber density of 0.005 to 0.20 g/cm$^3$ or preferably 0.007 to 0.07 g/cm$^3$. When the convex portion 2 has a fiber density less than 0.005 g/cm$^3$, the empty weight of liquid included in the convex portion 2 or an external pressure not only may cause the convex portion 2 to be easily crushed but also may cause once-absorbed liquid to return to the skin. When the convex portion 2 has a fiber density greater than 0.20 g/cm$^3$, liquid delivered to the convex portion 2 may be difficult to move to the lower side and cause accumulated liquid in the convex portion 2, resulting in the user experiencing a wet sensation.

With regard to the distribution of fiber density in a peripheral region from the substantial center of the side section of the open area 3 in the longitudinal direction to both ends, a fiber density gradually increases from the center of the side section of the open area 3 in the longitudinal direction to both ends of the open area 3 in the longitudinal direction. Specifically, the fiber density of the side section of the convex portion 2 having contact with the side section of the open area 3 in the longitudinal direction is gradually increases toward both ends of the open area 3 in the longitudinal direction. The reason is that, with an increase in the size of the open area 3, the amount of the fibers 101 blown to the joining portion 4 with fluid, mainly composed of gas, is also increased.

The nonwoven fabric 180 is also structured so that a percent open area measured from a face including the groove portion 1 and the convex portion 2 is less than a percent open area measured from another face opposite to the face including the groove portion 1 and the convex portion 2.

The fiber web 100 transported on the supporting member 240 (which will be described later) moves, by gravity force, to a surface opposite to a surface at which the fiber 101 is blown with fluid, mainly composed of gas, causing a tendency where fibers close to the opposite face have a smaller distance therebetween. On the other hand, the distance among fibers tends to increase in a range from a surface facing the supporting member 240 to the surface blown with fluid, mainly composed of gas.

By being blown with fluid, mainly composed of gas, some fibers 101 close to the supporting member 240 are pushed to the supporting member 240 and are directed to the flat surface of the supporting member 240. This further reduces the distance between fibers to easily provide closely-spaced fibers. When the closely-spaced fibers are subjected to heat treatment such as an oven processing, fibers are heat-sealed to reduce the degree of freedom of the fibers 101 in order to reduce the amount of open area between fibers of the other surface of the nonwoven fabric 180.

On the other hand, in a range from the supporting member 240-side face to a surface blown with fluid, mainly composed of gas, fibers are prevented from being excessively crushed and the fluid, mainly composed of gas, in the convex portion 2 is bounced from the supporting member 240 to cause some of the fibers 101 to be vertical to the supporting member 240. When such fibers are heat-sealed, the cross section of the fiber web 100 has a greater percent open area.

Percent open area is a percent of an area not occupied by fibers to the total area. The percent open area is measured according to the following method.

The percent open area is measured by a digital microscope VHX-100 made by KEYENCE CORPORATION.

(1) First, set a sample on an observation stand of a measurement device so that the direction along the groove portion 1 and the convex portion 2 is in the longitudinal direction.

(2) At an apex of the convex portion 2, a protruding surface of the convex portion 2 and an opposite surface to the protruding surface of the convex portion 2 are subjected to the following measurement, respectively.

(3) Appropriately set a lens magnification of the measurement device and a magnification of on a screen of a personal computer to focus the lens to fibers at the front side of the sample excluding fibers that protrude from the front of the sample in an irregular manner.

(4) Thereafter, appropriately set the photographing depth (depth) to create a 3D image of the sample.

(5) Convert the 3D image into a 2D image to planarize the set volume in order to identify the space in the sample range.

(6) Subject the 2D image to a binarization process to convert the portions containing fibers to white and to convert portions not containing fibers to black.

(7) Invert the colors to convert portions not containing fibers to white and then measure the white area, for example.

Based on a magnification of ×30 and a photographing depth of 220 µm (which means one photograph per 20 µm and a total of 11 photographs) to measure an average value based on the measurement of n=10.

The percent open area is calculated according to the following equation.

Percent Open Area (%)=(total of open area (mm$^2$)/ measured area (mm$^2$))×100

The percent open area can be calculated from (Total of pen area at measurement/Enlargement magnification at measurement), and the measured area can be calculated from (Measured area at measurement/Enlargement magnification at measurement).

A greater percent open area indicates a greater distance between fibers. Thus, a greater percent open area will allow fibers to more easily and provides the fibers with a greater degree of freedom. Furthermore, when nonwoven fabric is structured so that a part thereof includes a wide distance between fibers by an opening processing or the like, the nonwoven fabric has a greater open area per unit area and thus the entire surface of the nonwoven fabric to which fluid, mainly composed of gas, is blown can have a wide distance between fibers. Thus, when the nonwoven fabric is used as an absorbent article for example, resistance caused when predetermined liquid such as excretory substance passes the nonwoven fabric 180 can be entirely reduced to promote the delivery of liquid to absorber material or the like.

The open area per unit area refers to a ratio of the total area without fiber to the number of areas without fiber within a predetermined area. The open area can be calculated as follows: Open area $(mm^2/pc)$=(total of open area $(mm^2)$/number of open area (pc))

A difference between a percent open area measured from the protruding surface of the convex portion 2 and a percent open area measured from a surface opposite to the protruding surface of the convex portion 2 is 5 to 100%, preferably 5 to 80%, or more preferably 15 to 40%.

The percent open area measured from the protruding surface of the convex portion 2 is exemplarily 50 to 100%, preferably 50 to 90%, or more preferably 50 to 80%.

A open area per unit area measured from the protruding surface of the convex portion 2 is exemplarily 3000 $\mu m^2$ or more, preferably 3000 to 30000 $\mu m^2$, or more preferably 5000 to 20000 $\mu m^2$.

1.4. Basis Weight of Web

Specifically, an average basis weight of a web of the entire nonwoven fabric 180 is exemplarily 10 to 200 $g/m^2$ or preferably 20 to 100 $g/m^2$. When the nonwoven fabric 180 is used as a surface sheet of an absorbent article with an average basis weight of web that is less than 10 $g/m^2$ for example, the nonwoven fabric 180 may be easily broken during use. When the nonwoven fabric 180 has an average basis weight of web that is greater than 200 $g/m^2$, there may be a case where liquid delivered thereto is not smoothly transferred.

As described above, the convex portion 2 is structured so that the groove portion 1 has a lower basis weight of web than that of the fiber 101. Specifically, the convex portion 2 may exemplarily have a basis weight of web of 15 to 250 $g/m^2$ or preferably 20 to 120 $g/m^2$. When the convex portion 2 has a basis weight of web that is less than 15 $g/m^2$, the empty weight of liquid included in the convex portion 2 or an external pressure not only tends to easily crush the convex portion 2 but also cause once-absorbed liquid to return to the surface and come into contact with the skin. When the convex portion 2 has a basis weight of web that is greater than 250 $g/m^2$, liquid delivered to the convex portion 2 may be difficultly moved to the lower side to cause accumulated liquid in the convex portion 2, resulting in the user experiencing a wet sensation.

The groove portion 1 has an average basis weight of web that is less than an average basis weight of web of the entire structure including the groove portion 1 and the convex portion 2. Specifically, the bottom section of the groove portion 1 exemplarily has an average basis weight of web of 3 to 150 $g/m^2$ or preferably 5 to 80 $g/m^2$. When the bottom section of the groove portion 1 has an average basis weight of web that is less than 3 $g/m^2$, the nonwoven fabric 180 may easily be broken during use. When the bottom section of the groove portion 1 has an average basis weight of web that is greater than 150 $g/m^2$, liquid delivered to the groove portion 1 may be difficultly move to the lower side (the other surface) to cause accumulated liquid in the groove portion 1, resulting in the user experiencing a wet sensation.

Furthermore, the entire groove portion 1 has an average basis weight of web that is less than an average basis weight of web of the entire convex portion 2. Specifically, the entire groove portion 1 has an average basis weight of web of no greater than 90% of the basis weight of web of the convex portion 2, preferably 3 to 90% of the basis weight of web of the convex portion 2, or more preferably 3 to 70% of the basis weight of web of the convex portion 2. When the entire groove portion 1 has an average basis weight of web that is greater than 90% of the basis weight of web of the convex portion 2, resistance caused when liquid dropped to the liquid groove portion 1 moves to the lower side of the nonwoven fabric 180 (the other surface side) may be increased to cause liquid to overflow from the groove portion 1. When the bottom section of the groove portion 1 has a basis weight of web that is less than 3% of the basis weight of web of the convex portion 2, the nonwoven fabric 180 may easily be broken during use.

1.5. Others

When the nonwoven fabric 180 of this embodiment is used to absorb or to allow permeation of predetermined liquid for example, the groove portion 1 allows the liquid to permeate and the convex portion 2 has a porous structure and thus is difficult to retain the liquid. The open area 3 provided in the groove portion 1 can allow not only liquid but also solid substance to permeate.

The groove portion 1 includes the open area 3 and thus has a suitable structure through which liquid or solid substance can permeate. Furthermore, many fibers 101 located at the bottom section of the groove portion 1 oriented in the width direction can prevent liquid from excessively flowing in the longitudinal direction of the groove portion 1 and expanding over a wide area. In spite of the groove portion 1 having a low average basis weight of web, the joining portion 4 has a high fiber density to orient the fibers 101 in the width direction of the groove portion 1 (CD orientation), thus improving the strength of the nonwoven fabric 180 in the width direction (CD strength). Thus, in spite of the existence of the open area 3 having a relatively large size, the strength in the width direction can be improved.

The groove portion 1 has a percent content of laterally orientated fibers per unit area that is higher than that of the convex portion 2. At the side section of the convex portion 2, a percent content of longitudinally orientated fibers per unit area that is higher than that of the center part of the convex portion 2. The convex portion 2 includes the fibers 101 oriented in the thickness direction in a greater amount than that of the fibers 101 included in the groove portion 1. Even when the convex portion 2 is applied with a load in the thickness direction for example to reduce the thickness of the convex portion 2 and when the load is released, this allows the convex portion 2 to easily maintain their original height due to the rigidity of the fibers 101 oriented in the thickness direction. Specifically, nonwoven fabric having a high compression recovery characteristic can be obtained.

1.6. Manufacture Method

With reference to FIG. 3 to FIG. 9, a method for manufacturing the nonwoven fabric 180 of this embodiment will be described. First, the fiber web 100 is placed on an upper face of the supporting member 240 as a air permeable supporting member. In other words, the fiber web 100 is supported by the supporting member 240 from the lower side.

Then, the supporting member 240 supporting the fiber web 100 is moved in a predetermined direction to blow gas to the upper face of the fiber web 100 being moved to manufacture the nonwoven fabric 180 of this embodiment.

The supporting member 240 is exemplarily a supporting member as shown in FIG. 3 in which the upper face of the mesh supporting member 210 has thereon a plurality of elongated members 245 with a predetermined interval therebetween so that the elongated members 245 are substantially in parallel to one another.

An elongated member 245 is an impervious section that does not allow fluid, mainly composed of gas, to permeate. When fluid, mainly composed of gas, is blown to the elongated member 245, the fluid flows in a different direction. The fluid, mainly composed of gas, thus blown and/or the fluid, mainly composed of gas, flowing in a different direction by the elongated member 245 move(s) the fibers 101 to form the open area 3 and the joining portion 4.

This will be described in detail. In a region blown with the fluid, mainly composed of gas, longitudinal orientated fibers in the region are blown to a region adjacent to the region to form a recessed portion in the thickness direction, thereby providing a plurality of groove portions.

Then, a plurality of groove portions 1 has therebetween convex portions 2. The fibers 101 blown from the groove portion 1 allows the side section 8 of the convex portion 2 to have a greater fiber density and also allows the side section 8 to include longitudinally orientated fibers with a greater percent content.

At the same time, fluid, mainly composed of gas, blown to the groove portion 1 flows in a different direction by the elongated member 245. Then, the blown fluid, mainly composed of gas, and/or the fluid, mainly composed of gas, flowing in a different direction cause(s) longitudinally orientated fibers to be blown to the convex portion 2 and cause(s) laterally orientated fibers to be blown to the front and rear sides of the predetermined blowing direction, thereby providing the open area 3 and the joining portion 4.

In order to provide the nonwoven fabric 180 having the open area 3, a different supporting member also may be used. Depending on a supporting member to be used, the size or arrangement of the groove portion 1, the convex portion 2, the open area 3, and the joining portion 4 for example can be changed.

For example, a supporting member as shown in FIGS. 3A and 3B, in which a predetermined mesh member has thereon impervious sections arranged with a predetermined pattern or a supporting member as shown in FIG. 5 in which predetermined hole sections are formed among intermeshed wires may be used.

In addition to the member in which the predetermined mesh member has thereon impervious sections arranged with a predetermined pattern as described above, another supporting member also may be used in which the size or arrangement of the elongated member 245 as an impervious section is appropriately changed. An impervious section can be provided not only by the structure shown in FIGS. 3A and 3B in which the elongated members 245 are placed on one surface of the mesh supporting member 210 but also by filling holes in a mesh as a pervious section (e.g., by filling the holes by solder or resin) for example.

A supporting member 275 as shown in FIG. 5 is a supporting member in which predetermined hole sections are formed among intermeshed wires. The supporting member 275 is, for example, a spiral intermeshed air permeable net in which wires 276 having a predetermined thickness arranged to be substantially in parallel with one another are wound with wires 277 having a different predetermined thickness in a spiral manner so that the plurality of wires 276 are bridged.

In the supporting member 275, the wire 276 and wire 277 function as an impervious section. Portions in the supporting member 275 surrounded by the wire 276 and wire 277 are hole sections 278 functioning as a pervious section.

In the case of the supporting member as described above, air permeability can be partially changed by partially changing the intermeshing method, the thickness of a thread, or the shape of a thread. For example, such a supporting member may be exemplarily obtained in which the wire 276 of a circular stainless steel wire and the wire 277 of a flat stainless steel thread are spirally intermeshed.

However, the wire 276 and wire 277 functioning as an impervious section (intersecting points of the wires in particular) in the structure as described above exemplarily have an air permeability that is no greater than 90% of the air permeability of the hole section 278 as a pervious section, preferably 0 to 50%, or more preferably 0 to 20%. The term "0%" herein means air substantially cannot pass through.

Here, the nonwoven fabric 180 is formed by the nonwoven fabric manufacture apparatus 90 by sequentially moving the fiber web 100 in a predetermined direction. The nonwoven fabric manufacture apparatus 90 is an apparatus for manufacturing the nonwoven fabric 180 of this embodiment that includes: a air permeable supporting member 200 for supporting the fiber web 100 as a fiber assembly from one surface side; a blowing section 910 and an air supply section (not shown) as a blowing means for blowing, from the other surface side of the fiber web 100 as the fiber assembly, fluid, mainly composed of gas, to the fiber web 100 as a fiber assembly supported by the air permeable supporting member 200 from the one surface side; and a conveyer 930 as a transportation means for transporting the fiber web 100 as a fiber assembly in a predetermined direction F.

The conveyer 930 includes: an air permeable belt section 939 that has a ring-like shape extending in the lateral direction on which the air permeable supporting member 200 is placed; and rotation sections 931 and 933 that are provided at the inner side of the air permeable belt section 939 having a ring-like shape extending in the lateral direction and that are provided at both ends in the longitudinal direction to rotate the ring-like air permeable belt section 939 in a predetermined direction.

As described above, the conveyer 930 transports the fiber web 100 in the predetermined direction F via the air permeable supporting member 200 supported from the lower face. Specifically, as shown in FIG. 6, the fiber web 100 is transported to move under the blowing section 910. The fiber web 100 is also transported to move through a heater section 950 as a heating means in which both side faces are opened.

As shown in FIG. 8, the blowing means includes an air supply section (not shown) and the blowing section 910. The not shown air supply section is connected to the blowing section 910 via an air supply pipe 920. The air supply pipe 920 is connected to the upper side of the blowing section 910 so that air can be supplied there through. As shown in FIG. 9, the blowing section 910 includes a plurality of blowing openings 913 arranged with a predetermined interval there between.

Air supplied from the not shown air supply section via the air supply pipe 920 to the blowing section 910 is blown from a plurality of blowing openings 913 formed in the blowing section 910. Gas blown from the plurality of blowing openings 913 is continuously blown to the upper face of the fiber web 100 supported by the lower face of the air permeable supporting member 200. Specifically, gas blown from the plurality of blowing openings 913 is continuously blown to the upper face of the fiber web 100 moved by the conveyer 930 in the predetermined direction F.

An air-evacuation section 915 is placed under the blowing section 910 and is positioned at the lower side of the air permeable supporting member 200. The air-evacuation section 915 evacuates gas blown from the blowing section 910 to pass the air permeable supporting member 200 for example. By the air evacuation force by this air-evacuation section 915, the fiber web 100 also can be positioned as if the fiber web 100 adheres to the air permeable supporting member 200. Furthermore, the fiber web 100 also can be transferred to the heater section 950 while the fiber web 100 including therein more groove-like shapes (e.g., concavities and convexities)

formed by airflow by air evacuation. In this case, the fiber web 100 from which air is being evacuated is preferably transferred to the heater section 950 simultaneous with the formation of such groove-like shapes by airflow.

By evacuating blown fluid, mainly composed of gas, by the air-evacuation section 915, the fluid, mainly composed of gas, can be prevented from excessively being redirected from the air permeable supporting member 200 and unintentionally deforming the shape of the fiber web 100.

Fluid, mainly composed of gas, may be evacuated in such a manner that the fibers 101 in a region blown with fluid, mainly composed of gas, are pushed to the supporting member.

It is noted that the convex portion 2 can have a different shape by adjusting an air volume, a temperature or evacuation amount of blown fluid, mainly composed of gas, the air permeability of a supporting member, or the basis weight of web of the fiber web 100 for example. For example, the back face of the convex portion 2 in the nonwoven fabric 115 (nonwoven fabric 180) is formed to follow the shape of the air permeable supporting member 200 for example when an average amount of fluid, mainly composed of gas, is blown and an amount of fluid, mainly composed of gas, is evacuated or when a greater amount of fluid, mainly composed of gas, is evacuated for example. Thus, when the air permeable supporting member 200 is flat, the back face (i.e. face opposite to the face of the nonwoven fabric 115 (nonwoven fabric 180) including the groove portion 1 and convex portion 2) has a substantially flat surface.

Thus, by evacuating fluid, mainly composed of gas, from the lower side of the air permeable supporting member 200, fibers in a region blown with fluid, mainly composed of gas, are moved while being pushed to the air permeable supporting member 200, thus causing accumulation of fibers toward the air permeable supporting member 200. In the convex portion 2, blown fluid, mainly composed of gas, is redirected from the air permeable supporting member 200 to partially cause fibers to become orientated in the thickness direction.

Fluid, mainly composed of gas, blown from the blowing openings 913 may be at room temperature. However, in order to provide superior molding characteristics of a groove portion (concavity and convexity) or an open area for example, the fluid preferably has a temperature equal to or greater than at least the softening point of the thermoplastic fiber constituting the fiber assembly or preferably in a range of +50 degrees to −50 degrees of the melting point. The reason is that softened fibers have a deteriorated repulsive force and thus fibers rearranged by airflow or the like can be easily retained while a further higher temperature causes fibers to be h eat-sealed to one another and thus a groove portion (concavity and convexity) or the like can be maintained in a further easier manner. Thus, fibers including therein a groove portion (concavity and convexity) or the like can be more easily transferred into the heater section 950.

In the heater section 950 as a heating means, both ends in the predetermined direction F are opened. Thus, the fiber web 100 (nonwoven fabric 120) placed on the air permeable supporting member 200 moved by the conveyer 930 is continuously moved through a heating space provided in the heater section 950 such that the fiber web 100 stays in the heating space for a predetermined time. For example, when the fibers 101 constituting the fiber web 100 (nonwoven fabric 180) include thermoplastic fiber and are heated by this heater section 950, nonwoven fabric 115 can be obtained in which the fibers 101 are bound to one another.

The air permeable supporting member 200 can be appropriately changed depending on nonwoven fabric to be manufactured. When the nonwoven fabric 180 of this embodiment is manufactured for example, the above-described supporting member 240 can be used as the air permeable supporting member 200.

When the above-described supporting member 240 is used as a air permeable supporting member, the supporting member 240 in which the fiber web 100 is placed on the upper face is moved in a direction substantially orthogonal to the longitudinal direction of the elongated member 245. As a result, gas is continuously blown to the upper face of the fiber web 100 in a direction substantially orthogonal to the elongated member 245. Specifically, the groove portion 1 is formed in a direction substantially orthogonal to the elongated member 245. Then, the open area 3 (which will be described later) is formed at a position at which the elongated member 245 intersects with the groove portion 1.

The size of the open area 3 or a pitch therebetween can be arbitrarily determined based on the shape of the impervious section of the supporting member (e.g., the elongated member 245 of FIGS. 3 and 4, the wire 276 of FIG. 5) and the shape of the blowing opening 913. Specifically, the MD size of the open area 3 (size in the longitudinal direction) depends on the MD size (longitudinal direction size) of the impervious section of each supporting member while the CD size of the open area 3 (width direction size) depends on the CD size of the blowing opening 913 (width direction size). The MD pitch of the open area 3 (i.e., a length between the centers of adjacent open areas 3 in the longitudinal direction) depends on the MD pitch of the impervious sections of each supporting member (i.e., a length between the centers of adjacent impervious sections in the longitudinal direction). By appropriately changing these factors, the open area 3 having an intended size or pitch can be formed. It is noted that the shape of the blowing opening may be a circle, ellipse, square, or rectangle for example. In order to increase the CD size of the open area 3 (length in the width direction), a rectangular or elliptical shape extending in the lateral direction is preferred.

As descried above, the elongated member 245 is an impervious member through which, gas blown from the upper side cannot move to the lower side for example. In other words, gas blown to the elongated member 245 flows in a different direction.

The elongated member 245 also prevents the fibers 101 in the fiber web 100 from moving to the lower side of the supporting member 240.

Thus, the fibers 101 constituting the fiber web 100 are moved by gas blown from the upper face of the fiber web 100 gas and/or blown gas passing through the fiber web 100 and flowing in a different direction by the elongated member 245.

For example, the fibers 101 in a region blown with gas are moved to a region adjacent to the region. Thus, the region blown with gas is moved in a predetermined direction.

Consequently, the fibers 101 in a region blown with gas are moved to a side region continuous from the region in the predetermined direction.

As a result, the groove portion 1 is formed and the fibers 1 in the bottom section of the groove portion 1 are moved so as to be oriented in the width direction. Furthermore, the groove portion 1 and the groove portion 1 have therebetween the convex portion 2 to provide the side section of the convex portion 2 with an increased fiber density to orient the fibers 101 in the longitudinal direction.

Furthermore, blown gas which passes through the fiber web 100 and which flows in a different direction by the elongated member 225 moves the fibers 101 constituting the fiber web 100 in a different direction from the above direction.

The mesh supporting member 210 and the elongated member 245 constituting the supporting member 240 regulate the movement of the fibers 101 to the lower face of the supporting member 240. Thus, the fibers 101 are moved in a direction along the upper face of the supporting member 240.

In particular, the gas blown to the elongated member 245 flows in a different direction along the elongated member 245. The gas thus flowing in a different direction causes the fibers 101 provided at the upper face of the elongated member 245 to move from the upper face of the elongated member 245 to a peripheral region, thereby providing the open area 3 having a predetermined shape. At the same time, one or two or more of the orientation, the density variation, or a basis weight of web of the fibers 101 is/are adjusted.

Furthermore, a single supporting member can be used to manufacture nonwoven fabric having different open area 3, groove portion 1, or convex portion 2 of a different arrangement, basis weight of web, or fiber density by adjusting the temperature, amount or strength of the fluid, mainly composed of gas, blown to the fiber web 100 or by adjusting the travel speed of the fiber web 100 by the transportation means to adjust the tension for example. It is also possible to use different supporting members to manufacture nonwoven fabric having the same open area 3, groove portion 1, or convex portion 2 of an identical arrangement, basis weight of web or fiber density by adjusting the temperature, amount or strength of the fluid mainly composed of gas blown to the fiber web 100 or by adjusting the travel speed of the fiber web 100 by the transportation means to adjust the tension for example.

When the above-described supporting member 275 (FIG. 5) is used and fluid, mainly composed of gas, is blown to an intersecting point of the wire 276 and the wire 277 at the supporting member 275 in the groove portion 1, the fluid, mainly composed of gas, flows in a different direction by the intersecting point. Consequently, the fibers 101 supported by the intersecting point are blown toward the front and rear and left and right sides to form the open area 3.

Then, the fibers 101 in a region in the groove portion 1 supported by parts other than the intersecting point are pushed down to the supporting member 275 and thus are suppressed from moving to the lower side. The wire intersecting point also moves laterally orientated fibers, thereby forming the joining portion 4.

A region functioning as a pervious section exemplarily has an air permeability of 10000 to 60000 cc/cm$^2$·min or preferably 20000 to 50000 cc/cm$^2$·min. However, when a air permeable supporting member includes a pervious section obtained by cutting a metal plate for example, the plate has no resistance to fluid, mainly composed of gas, and thus the pervious section in this case may have air permeability equal to or higher than the above-described values.

A supporting member to be used is preferably structured so that a region functioning as an impervious section has a greater surface slipping property than that of a region functioning as a pervious section. The reason is that a greater surface slipping property allows the fibers 101 existing at a part at which a region blown with fluid, mainly composed of gas, intersects with an impervious section to easily move and thus the open area 3 and the joining portion 4 can more easily be formed.

2. Other Embodiments

Hereinafter, a modification of the embodiment of the nonwoven fabric of the present invention will be described. In the following modification, the same components as those of the first embodiment will not be further described and have the same reference numerals as those of Embodiment 1.

With reference to FIGS. 10 to 13, the second to fourth embodiment of the nonwoven fabric of the present invention will be described. The second embodiment is different from the first embodiment in a surface opposite to a surface including a convex portion of nonwoven fabric. The third embodiment is different to the first embodiment in the entire shape of nonwoven fabric. The fourth embodiment is different to the first embodiment in a convex portion of nonwoven fabric.

2.1. Embodiment 2

With reference to FIG. 10, the second embodiment of the nonwoven fabric of the present invention will be described.

As shown in FIG. 10, nonwoven fabric 182 of this embodiment is different from the nonwoven fabric of the first embodiment in a surface of the nonwoven fabric 182 opposite to a face including the groove portion 1 and the convex portion 2. The following section will describe the difference between that of the first and second embodiments.

2.1.1. Nonwoven Fabric

The nonwoven fabric 182 of this embodiment is structured so that one surface includes the groove portions 1 and the convex portions 2 are alternately arranged so as to be in parallel to one another. The other surface side of nonwoven fabric 182 includes a region constituting a bottom face of the convex portion 2 formed to protrude in a direction along which the convex portion 2 protrudes. In other words, the nonwoven fabric 182 is structured so that the other surface of the nonwoven fabric 182 includes a region constituting the bottom face of the convex portion 2 at the one surface that is shaped to form a concave section. The region at the other surface constituting the bottom face at the groove portion 1 of the one surface protrudes in a direction opposite to the convex portion of the one surface to form a convex portion.

2.1.2. Manufacture Method and Supporting Member

The second embodiment has the same method for manufacturing the nonwoven fabric 182 as that of the first embodiment. The second embodiment can use the same supporting member for manufacturing the nonwoven fabric 182 as the supporting member 240 of the first embodiment.

The nonwoven fabric 182 supported by the supporting member 240 from the lower face side is blown with fluid, mainly composed of gas, simultaneous with evacuation of fluid, mainly composed of gas, from the lower side of the supporting member 240. An amount of the evacuated fluid, mainly composed of gas, is less than an amount of blown fluid, mainly composed of gas. When an amount of blown fluid, mainly composed of gas, is greater than an amount of evacuated fluid, mainly composed of gas, blown fluid, mainly composed of gas, collides with the supporting member 240 as an air permeable supporting member for example to be partially bounced. This provides the lower face (bottom face) at a back side of the convex portion 2 that is formed to protrude in the same direction as that of the upper face of the convex portion 2. In other words, the lower face protrudes in proportion with the convex shape provided by the protruded convex portion 2.

When the convex portion 2 of the nonwoven fabric 182 is curved to the upper face, a region of another face of the groove portion 1 adjacent to the convex portion relatively protrudes to form a convex portion protruding to the lower face. Specifically, a protruded region protruding in an opposite direction to a direction along which the convex portion protrudes is formed. Thus, the nonwoven fabric 182 is composed by a convex portion and a groove portion.

2.2. Embodiment 3

With reference to FIG. 11 and FIG. 12, the third embodiment of the nonwoven fabric of the present invention will be described.

2.2.1. Nonwoven Fabric

As shown in FIG. 11, nonwoven fabric 184 of the third embodiment is different to the nonwoven fabric of the first embodiment in that the nonwoven fabric 184 protrudes in a wave-like manner. The following section will mainly describe the difference between that of the first and third embodiments.

The nonwoven fabric 184 of the third embodiment is structured so that the entire nonwoven fabric has an undulating surface substantially orthogonal to a direction along which the groove portion 1 and the convex portion 2 extend.

2.2.2. Manufacture Method

According to the third embodiment the manufacture of the nonwoven fabric 184 is by the same method as that of the first embodiment except for the shape of a supporting member, as an air permeable supporting member. Specifically, a supporting member 280 of the third embodiment is structured, as shown in FIG. 12, so that the upper face of a mesh supporting member 260 includes a plurality of elongated members 285 arranged with a predetermined interval so as to be substantially in parallel to one another.

The supporting member 280 of the third embodiment is structured, as shown in FIG. 12, so that any one of the longitudinal direction or lateral direction of the supporting member 280 has an undulating surface in a direction in parallel with the longitudinal or lateral direction. The supporting member 280 is composed by mesh supporting members 260 each of which includes a plurality of hole sections 263 having a small hole diameter. Thus, gas blown from the upper face of the fiber web 100 passes through the mesh supporting member 260. This mesh supporting member 260 does not change the direction of fluid, mainly composed of gas, blown thereto and does not move the fibers 101 to the lower side of the mesh supporting member 260.

The mesh supporting member 260 constituting the supporting member 280 also has, at the upper face thereof, the elongated members 285 that function as an impervious section through which fluid, mainly composed of gas, blown from the upper face cannot pass and flows in a different direction. As a result, fluid, mainly composed of gas, blown to the elongated member 285 and/or fluid, mainly composed of gas, blown to the elongated member 285 to flow in a different direction move(s) the fibers 101, thereby providing the open areas 3.

Furthermore, the mesh supporting member 260 constituting the supporting member 280 having a curved surface allows fluid, mainly composed of gas, blown from the upper face of the fiber web 100 to form the fiber web 100 to have a curved shape following the shape of the supporting member 280.

The nonwoven fabric 184 of the third embodiment can be obtained by moving the fiber web 100 along an X axis direction while blowing fluid, mainly composed of gas, to the fiber web 100 placed on the upper face of the supporting member 280.

The supporting member 280 can have an arbitrary undulating surface. For example, a pitch between apex portions of protrusions constituting the undulating surface in the direction X shown in FIG. 12 may exemplarily be 1 to 30 mm or preferably 3 to 10 mm. A difference in height between an apex portion and a bottom section constituting the undulating surface of the supporting member 280 may exemplarily be 0.5 to 20 mm or preferably 3 to 10 mm for example. The cross sectional shape of the supporting member 280 in the direction X is not limited to the one shown in FIG. 12. For example, a cross-sectional shape in which substantially triangular shapes are continued so that the respective apexes of protrusions have an acute angle or a cross-sectional shape in which substantially rectangular concavity and convexity are continued so that the respective apexes of protrusions are substantially flat also may be used for example.

The nonwoven fabric 184 of the third embodiment can be manufactured by the above-described nonwoven fabric manufacture apparatus 90. The manufacture of the nonwoven fabric 184 by the nonwoven fabric manufacture apparatus 90 can be performed based on the description in the first embodiment for the method for manufacturing the nonwoven fabric 180 and the nonwoven fabric manufacture apparatus 90 for example.

2.3. Embodiment 4

With reference to FIG. 13, the fourth embodiment of the nonwoven fabric of the present invention will be described.

As shown in FIG. 13, nonwoven fabric 186 of the fourth embodiment is different from the nonwoven fabric of the first embodiment in that the second convex portion 22 is provided that has a different height in the thickness direction from that of the convex portion 2 formed at one surface of the nonwoven fabric 186. The following section will describe the difference between that of the first and fourth embodiments.

2.3.1. Nonwoven Fabric

The nonwoven fabric 186 is structured so that one surface includes a plurality of groove portions 1 arranged in parallel to one another. The plurality of groove portions 1 have there between a plurality of convex portions 2 and a plurality of the second convex portions 22 alternately arranged, respectively. The convex portions 2 and the second convex portions 22 are arranged in parallel to one another as in the plurality of groove portions 1. Each groove portion 1 includes the open area 3 and joining portion 4.

The convex portion 2 and the second convex portion 22 are regions in the fiber web 100 that are not blown with fluid, mainly composed of gas, and that are proportionally protruded by the formation of the groove portion 1. In the nonwoven fabric 186, the second convex portion 22 has a height in the thickness direction and a length in the width direction both lower than those of the convex portion 2 for example. However, the second convex portion 22 has the same fiber density variation, fiber orientation, and basis weight of web as those of the convex portion 2 for example.

The nonwoven fabric 186 includes the convex portions 2 and the second convex portions 22 in such a manner that a plurality of groove portions 1 arranged in parallel to one another have there between the convex portion 2 or the second convex portion 22 and the convex portion 2 is adjacent to the second convex portion 22 so that the groove portion 1 is sandwiched there between. In other words, the second convex portion 22 is adjacent to the convex portion 2 so that the groove portion 1 is sandwiched there between. Specifically, the convex portion 2 and the second convex portion 22 in this order or a reverse order alternately sandwich the groove portion 1. Specifically, the convex portion 2, groove portion 1, the second convex portion 22, the groove portion 1, and the convex portion 2 are repeatedly arranged in this order. It is noted that the positional relation between convex portion 2 and the second convex portion 22 is not limited to this and at least a part of the nonwoven fabric 186 also can be formed so that the groove portion 1 is sandwiched by a plurality of convex portions 2, respectively or by a plurality of the second convex portions 22, respectively.

2.3.2. Manufacture Method and Supporting Member

The nonwoven fabric 186 of the fourth embodiment can be manufactured by the same manufacture method as that described in the first embodiment except for the blowing opening 913 of the nonwoven fabric manufacture apparatus 90 used for manufacturing the nonwoven fabric 186.

The nonwoven fabric 186 is obtained by moving the fiber web 100 placed on the upper face of the supporting member 240 while blowing fluid, mainly composed of gas, to the fiber web 100. When the fiber web 100 is blown with fluid, mainly composed of gas, the groove portion 1, the convex portion 2, the second convex portion 22, the open area 3, and the joining portion 4 are formed. These members can be arbitrarily formed by changing the blowing opening 913 of the nonwoven fabric manufacture apparatus 90 through which fluid, mainly composed of gas, is discharged.

For example, the nonwoven fabric 186 as shown in FIG. 13 can be formed by adjusting, for example, an interval between the blowing openings 913 from which fluid, mainly composed of gas, is blown. For example, by providing the blowing opening 913 with an interval there between that is less than an interval between the blowing openings 913 of the first embodiment, the second convex portion 22 can have a height in the thickness direction that is less than that of the convex portion 2. By providing the blowing openings 913 with an interval there between that is greater than an interval between the blowing openings 913 of the first embodiment, the second convex portion 22 also can have a height in the thickness direction that is greater than that of the convex portion 2. The blowing openings 913 are arranged among intervals so that a narrow interval and a wide interval are alternately provided. This provides the nonwoven fabric 186 in which the convex portion 2 and the second convex portion 22 are alternately provided in parallel to one another to sandwich the groove portion 1. However, an interval between the blowing openings 913 is not limited to this and may be arbitrarily determined based on the height of the convex portion 2 of a to-be-obtained nonwoven fabric and the arrangement of the second convex portions 22. The alternate arrangement of a narrow interval and a wide interval between which the blowing opening 913 is provided provides the nonwoven fabric 186 in which the convex portion 2 and the second convex portion 22 are alternately provided in parallel to one another to sandwich the groove portion 1.

The nonwoven fabric 186 of the fourth embodiment can be manufactured by the above-described nonwoven fabric manufacture apparatus 90. The manufacture of the nonwoven fabric 186 by the nonwoven fabric manufacture apparatus 90 can be performed based on the description in the first embodiment for the method for manufacturing the nonwoven fabric 180 and the nonwoven fabric manufacture apparatus 90 for example.

3. Illustrative Embodiment

Fiber Structure

In an illustrative embodiment, such cotton mixture is used that has a core-in-sheath structure of high density polyethylene and polyethylene terephthalate and an average fineness of 3.3 dtex and that includes fiber A having an average fiber length of 51 mm and being coated with hydrophilic solution oil and fiber B different from fiber A in being coated with water-repellent oil. The cotton mixture includes fiber A mixed with fiber B with a mixing ratio of 70:30 to provide a fiber assembly having a basis weight of web of 40 g/m$^2$.

Manufacture Conditions

In FIG. 9, the blowing opening 913 is a rectangular opening extending in the lateral direction that has a rectangular column-like cross section. The blowing opening 913 is sized to have a longitudinal length of 1.0 mm, a lateral length of 6.0 mm and a plurality of blowing openings 913 have there between a pitch of 14 mm. The blowing section 910 has a width of 500 mm and is blown with hot air at a temperature of 105 degrees C. and with an air volume of 1000 l/min.

A supporting body uses a stainless sleeve cut to have a rectangular shape having a length of 2 mm and a width of 70 mm that extends in the lateral direction and has rounded corners. In the sleeve, the patterns cut in the manner as described above are arranged in a lattice-like manner with an interval in the MD direction (longitudinal direction along which a groove portion or a convex portion extends) of 12 mm and an interval in the CD direction (lateral direction that is substantially orthogonal to the direction along which a groove portion or a convex portion extends) of 3 mm. The sleeve has a thickness of 0.5 mm.

The fiber assembly having the above-described fiber structure is spread-fibered by a card machine having a speed of 20 m/minute to prepare a fiber web. Then, the fiber web is cut to have a width of 450 mm. Then, the fiber web is transferred by an air permeable net (20 mesh) with a speed of 3 m/min. Then, the fiber web is blown with airflow at a temperature of 105 degrees C. and an air volume of 1200 l/min by the blowing section 910 and the blowing opening 913. Then, air is evacuated from the lower side of the air permeable net with the amount of air being evacuated being less than the amount of hot air being blown. Thereafter, the fiber web is transferred in an oven at a temperature of 125 degrees C. and a hot air volume of 10 Hz for about 30 seconds while being transferred by the air permeable net.

Result

Convex portion: The resultant convex portion shows a basis weight of web of 52 g/m$^2$, a length in the thickness direction of 3.8 mm, and a fiber density of 0.01 g/cm$^3$. One convex portion shows a width of 8.5 mm and a pitch of 14 mm.

Groove portion: The resultant groove portion shows an average basis weight of web of 11 g/m$^2$, a length in the thickness direction of 1.8 mm and a fiber density of 0.007 g/cm$^3$. One groove portion shows a width of 5.5 mm and a pitch of 14 mm.

Joining portion: The resultant joining portion shows a basis weight of web of 30 g/m$^2$, a length in the thickness direction of 1.8 mm, and a fiber density of 0.02 g/cm$^3$. One joining portion shows a width of 5.5 mm, a length of 2.1 mm, a pitch in the MD direction of 15.0 mm, and a pitch in the CD direction of 14.0 mm.

Open area: One resultant open area shows a width of 5.3 mm, a length of 11.5 mm, a pitch in the MD direction of 15.0 mm, and a pitch in the CD direction of 14.0 mm.

Shape: The convex portion, groove portion, open area, and joining portion are respectively formed and the back face of the convex portion protrudes in the same direction as that of the convex portion to fail to constitute the lowermost face of the nonwoven fabric. Along a direction in which the groove portion extends, the joining portions and the open areas are alternately provided. The open area has a rectangular shape extending in the longitudinal direction having an area of 61.0 mm² and having rounded corners.

4. Illustrative Application

The nonwoven fabric of the present invention can be used, for example, as a surface sheet for an absorbent article such as a sanitary napkin, liner or diaper. In this case, the convex portion may be provided in a skin-side face or in a back face. However, the convex portion provided in a skin-side face may reduce the area in which the nonwoven fabric comes into contact with skin and thus a wet feeling due to bodily fluid may be suppressed. The nonwoven fabric of the present invention also can be used as an intermediate sheet between a surface sheet of an absorbent article and absorber material. In this case, the area in which skin has contact with the surface sheet or the absorber material may be reduced and thus body fluid is suppressed from desorbing and coming into contact with the skin. The nonwoven fabric of the present invention also can be used as a side sheet of an absorbent article, an outermost sheet of a diaper, or a female tape of a hook fastener tape for example because the nonwoven fabric of the present invention can reduce the area having contact with skin and can provide a cushion feeling. The nonwoven fabric of the present invention also can be used for various products such as a wiper sheet for removing dust or scurf attached to a human body for example, a mask, or a nursing pad.

4.1. Surface Sheet of Absorbent Article

The nonwoven fabric of the present invention can be exemplarily used as surface sheets 301 and 302 of an absorbent article as shown in FIG. 14 and FIG. 15 for example. The surface sheets 301 and 302 have concavities and convexities. In the surface sheets 301 and 302, a concave section includes a plurality of open areas and a joining portion has a fiber density that is relatively higher than that of a convex portion. In this case, the nonwoven fabric is preferably arranged so that a surface, including the convex portion, faces towards human skin.

When the nonwoven fabric is used as the surface sheets 301 and 302 for an absorbent article, predetermined liquid excreted to the absorbent article is mainly delivered to the groove portions. The existence of the open areas allows, even when viscous liquid including solid substance for example is discharged to the nonwoven fabric, the liquid to be easily transferred via the open areas to the absorber material, thereby suppressing the liquid from expanding in the surface.

Furthermore, most fibers in the joining portion oriented in the width direction provide a high tensile strength in the width direction to prevent a situation where the surface sheets 301 and 302 are broken due to friction in the width direction while the absorbent article being worn by a user for example.

On the other hand, a side section of the convex portion has closely-spaced fibers and has a high rigidity. The longitudinally orientated fibers are oriented in the longitudinal direction with a high percent content. This prevents, even when a load is applied to the convex portions, the nonwoven fabric from being easily crushed and, even when the convex portions are crushed by a load, a high compression recovery characteristic is obtained.

This can maintain a small area having a contact with skin even when the posture of a user changes and changes the load being applied to the surface sheets 301 and 302. Thus, the intended tactile sensation can be maintained and, even when liquid once absorbed by the absorber material returns to skin, the liquid is suppressed from being attached to skin again.

4.2. Intermediate Sheet of Absorbent Article

The nonwoven fabric of the present invention also can be exemplarily used, as shown in FIG. 16, as an intermediate sheet 311 for an absorbent article for example. The intermediate sheet 311 is structured so that a concavity and a convexity are provided and a concave section includes a plurality of open areas and a joining portion has a fiber density that is relatively higher than that of a convex portion. In this case, the nonwoven fabric is preferably arranged so that a surface including the convex portion is at the surface sheet 310 side.

The nonwoven fabric of the present invention is structured so that a joining portion has a greater fiber density and most fibers in the joining portion are oriented in the width direction, thus providing a high tensile strength in the width direction. Even when the intermediate sheet 311 is subjected to a tensile load in the width direction due to the deformation of the absorbent article while the absorbent article being worn by a user, damage to the intermediate sheet 311 is prevented.

By placing the nonwoven fabric as the intermediate sheet 311 so that a surface including the convex portions is at the surface sheet 310 side, the surface sheet 310 and the intermediate sheet 311 can have there between a plurality of spaces. Furthermore, the intermediate sheet 311 including open areas allows, even when a large amount of liquid is excreted to the nonwoven fabric within a short time, the liquid can be immediately delivered to the absorber material while being less inhibited. Thus, the liquid can be prevented from returning to the surface sheet 310 and spreading over a wide area.

Even when liquid that passes the intermediate sheet 311 and is absorbed by the absorbent material returns to skin, a low contact ratio between the intermediate sheet 311 and the surface sheet 310 suppresses the liquid from returning to the surface sheet 310 and widely coming into contact with the skin.

The center part of the convex portion includes fibers oriented in the thickness direction in a greater amount than those in the side section and the groove portion and the intermediate sheet 311 has a convex portion having an apex that has a contact with the surface sheet 310. Thus, liquid left on the surface sheet 310 can be easily absorbed in the thickness direction. This suppresses the liquid from being left on the surface sheet 310.

Thus, the surface sheet 310 can have a spot property and causes less residual liquid thereon. Thus, liquid can be prevented from being attached to skin for a long time. Furthermore, the side section of the convex portion of the intermediate sheet 311 includes longitudinally orientated fibers oriented in the longitudinal direction with a high inclusion rate. Thus, liquid delivered from the surface sheet 310 to the side section can be guided in the longitudinal direction. Even when liquid is dispersed in the width direction in the intermediate sheet 311, this prevents the liquid from leaking from the absorbent article thus improving the absorption efficiency of the absorber material.

4.3. Outermost Section of Absorbent Article

The nonwoven fabric of the present invention also can be exemplarily used as an outermost section 321 for an absorbent article as shown in FIG. 17 for example. The outermost section 321 is structured so that concavities and convexities are provided, a concave section includes a plurality of open areas, and a joining portion has a fiber density that is relatively higher than that of a convex portion. In this case, the nonwoven fabric is preferably arranged so that a surface including the convex portion is at the outer side of the absorbent article.

The outermost section 321 is structured so that the surface including the convex portion is at the outer side of the absorbent article. Thus, when a hand touches the absorbent article during use for example, an improved feeling can be provided to the hand. The existence of the open areas in the groove portion provides superior air permeability.

5. Constituting Members

The following section will describe in detail the respective constituting members of the nonwoven fabric of the present invention.

5.1. Nonwoven Fabric

5.1.1. Fiber Assembly

A fiber assembly is provided to have a substantially sheet-like shape and is structured to include fibers having a degree of freedom. In other words, fibers in a fiber assembly have a degree of freedom from one another. The term "degree of freedom from one another" herein indicated that the fibers in a fiber web as a fiber assembly can be moved by fluid, mainly composed of gas. This fiber assembly can be obtained, for example, by blowing mixed fibers including a plurality of fibers to form a fiber layer having a predetermined thickness. This fiber assembly can be obtained, for example, by layering the respective plurality of different fiber to form fiber layers.

A fiber assembly of the present invention may exemplarily be, for example, a fiber web formed by the card method or a fiber web not yet heat-sealed to solidify the fibers. A fiber assembly of the present invention also may exemplarily be, for example, a web made by the air-laid method or a fiber web not yet heat-sealed to solidify fibers. A fiber assembly of the present invention also may exemplarily be, for example, a fiber web that is embossed by the point bond method and that is not yet heat-sealed to solidify the fibers. A fiber assembly of the present invention also may exemplarily be, for example, a fiber assembly that is spun by the span bond method and that is not yet embossed or a fiber assembly that is embossed and that is not yet heat-sealed to solidify fibers. A fiber assembly of the present invention also may exemplarily be, for example, a fiber web that is formed by the needle punch method and that is halfway interlaced. A fiber assembly of the present invention also may exemplarily be, for example, a fiber web formed by the span lace method and that is halfway interlaced. A fiber assembly of the present invention also may exemplarily be, for example, fiber web that is spun by the melt blown method and that is not yet heat-sealed to solidify fibers. A fiber assembly of the present invention also may exemplarily be, for example, a fiber assembly in which fibers are not yet solidified by solvent provided by the solvent welding method.

A fiber web in which fibers can be easily re-arranged by air (gas) may preferably be a fiber web made having a relatively long fiber that is made by the card method or a fiber web having fibers having a high degree of freedom to one another and having a not yet heat-sealed web provided only by inter-lacing. In order to provide nonwoven fabric by forming groove portions (concavities and convexities) by a plurality of air (gas) flows to subsequently retain the shapes, the through air method is preferred according to which a predetermined heating apparatus for example is used to heat a fiber assembly by an oven processing (heat processing) to heat-seal thermoplastic fibers included in the fiber assembly.

5.1.2. Fibers

Fibers constituting a fiber assembly (e.g., fibers 101 constituting fiber web 100) may be, for example, thermoplastic resin (e.g., low density polyethylene, high density polyethylene, straight-chain polyethylene, polypropylene, polyethylene terephthalate, modified polypropylene, modified polyethylene terephthalate, nylon, polyamide) for example and the respective resins may be used separately or in combination.

Such resins may be combined with complex shapes such as the core-in-sheath type in which the core component has a higher melting point than that of the sheath component, the core-in-sheath eccentric core type, or the side-by-side-type in which left and right components have different melting points. Alternatively, other shapes also may be used such as a variant type (e.g., hollow type, flat type, Y-type, C-type), a three-dimensional crimp fiber (e.g., potential crimp, apparant crimp), or a divided fiber divided by a physical load such as aqueous stream, heat, or embossing.

In order to form a three-dimensional crimp shape, predetermined apparant crimp fiber or potential crimp fiber can be mixed. The term "three-dimensional crimp shape" herein means a spiral shape, a zigzag shape, a Ω-like shape for example in which fibers are mainly oriented in the flat surface direction but some fibers are oriented in the thickness direction. As a result, the yielding strength of fibers themselves is applied in the thickness direction and thus the resultant nonwoven fabric is suppressed, even when being applied with an external pressure, from having a reduced volume. The spiral shape in particular allows the resultant nonwoven fabric applied with an external pressure to easily have an original shape. Thus, even when the volume is slightly reduced due to an excessive external pressure, such a spiral shape can easily have an original thickness when the external pressure is cancelled.

The term "apparant crimp fiber" is a collective term denoting previously crimped fibers (e.g., fibers shaped by a machine crimp, the ones having a core-in-sheath structure of an eccentric core type, the side-by-side type). The term "apparant crimp fiber" means fibers that are crimped when heated.

In a machine crimp, a continuous straight fiber after a fiber spinning can be controlled by the difference in the circumferential velocity of a line speed, heat, or pressurization. As the number of crimps per a unit length is higher, a yielding strength under an external pressure can be increased. For example, the number of crimps is 10 to 35/inch or preferably 15 to 30/inch.

Fibers shaped by heat shrinkage are composed of two or more resins each having different melting points. When such fibers are heated, the difference in the melting point causes a change in a heat shrinkage rate to cause a three-dimensional crimping of the fibers. Resin of such fibers has a cross section of the core-in-sheath structure of an eccentric core type or the side-by-side type in which left and right components have different melting points for example. Such fibers exemplarily have a heat shrinkage rate of, for example, 5 to 90% or preferably 10 to 80%.

A heat shrinkage rate can be measured according to the following method.
(1) A web of 200 g/m$^2$ is prepared by 100% of fiber to be measured.
(2) A sample cut to have a size of 250×250 mm is prepared.
(3) This sample is left in an oven at 145 degrees C. (418.15 K) for 5 minutes.
(4) The length after shrinkage is measured.

(5) The heat shrinkage rate is measured based on the difference in length before and after heat shrinkage.

When this nonwoven fabric is used as a surface sheet, the nonwoven fabric preferably has a fineness of 1.1 to 8.8 dtex in consideration of liquid permeation or texture, for example.

When this nonwoven fabric is used as a surface sheet, the fiber assembly may be composed of fibers such as, in order to absorb even a small amount of menstrual blood or sweat for example left on skin, cellulose-base hydrophilic fibers (e.g., pulp, chemical pulp, rayon, acetate, natural cotton). However, cellulose-base fibers difficultly discharge liquid once absorbed therein. Thus, cellulose-base fibers may be exemplarily mixed in a range from 0.1 to 5 mass % to the entire mixture for example.

When this nonwoven fabric is used as a surface sheet, the above-described hydrophobic synthetic fibers may be mixed with hydrophilic agent or water repellent agent or the like or may be coated in consideration of liquid permeation or reverting to wet state for example. Alternatively, the nonwoven fabric also may be subjected to corona processing or plasma processing to provide hydrophilic properties. Alternatively, the nonwoven fabric also may include water-repellent fibers. The term "water-repellent fibers" herein means fibers that have been subjected to a known water-repellent treatment process.

In order to provide whiter nonwoven fabric, the nonwoven fabric also may include, for example, inorganic filler (e.g., titanium oxide, barium sulfate, calcium carbonate). When the nonwoven fabric uses the core-in-sheath type complex fibers, such filler may be included only in the core or in both of the core and the sheath.

As described above, a fiber web in which fibers can be easily re-arranged by airflow is a fiber web made having a relatively long fiber that is made by the card method. In order to provide nonwoven fabric by forming groove portions (concavities and convexities) by a plurality of air flows to subsequently retain the shapes, the through air method is preferred according to which a fiber assembly is heated by an oven processing (heat processing) to heat-seal thermoplastic fibers. Fibers suitable for this manufacture method are preferably those having the core-in-sheath structure or side-by-side structure in order to heat-seal intersecting points of the fibers or are more preferably those having the core-in-sheath structure in which sheaths can be easily heat-sealed in a secure manner. In particular, core-in-sheath complex fibers consisting of polyethylene terephthalate and polyethylene or core-in-sheath complex fibers consisting of polypropylene and polyethylene are preferred. These fibers may be separately used or two or more types of fibers also may be combined. These fibers preferably have a fiber length of 20 to 100 mm or more preferably 35 to 65 mm.

5.2. Apparatus for Manufacturing Nonwoven Fabric 5.2.1. Fluid Mainly Composed of Gas Fluid mainly composed of gas of the present invention exemplarily may be, for example, gas adjusted to room temperature or a predetermined temperature or aerosol in which the gas includes solid substance or liquid fine particles.

Gas exemplarily may be, for example, air or nitrogen. Gas includes moisture from liquid (e.g., water vapor).

Aerosol means gas in which liquid or solid substance is dispersed including, for example, ink for coloration, softener for improving softness (e.g., silicon), hydrophilic property or water-repellent active agent for an antistatic purpose or for controlling a wetting property, inorganic filler (e.g., titanium oxide, barium sulfate) for improving a fluid energy, powder bond (e.g., polyethylene) for improving a fluid energy and for more securely maintaining the shape, in a heat processing, of concavities and convexities, antihistamine agent for itching prevention (e.g., diphenhydramine hydrochloride, isopropyl methyl phenol), moisturizing agent or disinfectant. Solid substance herein means to include a gel-like substance.

The temperature of fluid, mainly composed of gas, can be appropriately adjusted depending on the property of fibers constituting the fiber assembly or the shape of a to-be-manufactured nonwoven fabric.

In order to move fibers constituting a fiber assembly in a favorable manner for example, a certain level of high temperature fluid, mainly composed of gas, is preferred because it increases the degree of freedom of the fibers that constitute the fiber assembly. When a fiber assembly includes thermoplastic fibers, fluid, mainly composed of gas, can be at a temperature at which the thermoplastic fiber can be softened so that thermoplastic fibers placed in a region blown with the fluid, mainly composed of gas, for example can be softened or melt and can be subsequently cured again.

Using a temperature as described above, the shape of nonwoven fabric is retained when blown with fluid, mainly composed of gas, for example. The above temperature also provides strength to a fiber assembly (nonwoven fabric) to prevent, when the fiber assembly is moved by a predetermined transportation means, the fiber assembly from being damaged.

A flow rate of fluid, mainly composed of gas, can be appropriately adjusted. Specific examples of a fiber assembly in which fibers have a degree of freedom to one another include, for example, the fiber web 100 mainly having the core-in-sheath fibers in which the sheath is a high density polyethylene and the core is a polyethylene terephthalate, the fiber length is 20 to 100 mm or preferably 35 to 65 mm, the fineness is 1.1 to 8.8 dtex or preferably 2.2 to 5.6 dtex and has a fiber length of 20 to 100 mm or preferably 35 to 65 mm when using spread fiber by the card method or has a fiber length of 1 to 50 mm or preferably 3 to 20 mm when using spread fiber by the air-laid method. The fiber web 100 can be exemplarily adjusted to achieve 10 to 1000 g/m$^2$ or preferably 15 to 100 g/m$^2$. Fluid, mainly composed of gas, may be blown to the fiber web 100, for example, through the blowing section 910 (blowing opening 913, diameter of 0.1 to 30 mm or preferably 0.3 to 10 mm, pitch of 0.5 to 20 mm or preferably 3 to 10 mm, shape of a circle, an elliptic, or a rectangular shape) including the plurality of blowing openings 913 shown in FIG. 8 or FIG. 9 to blow hot air having a temperature or 15 to 300 degrees C. (288.15 K to 573.15 K) or preferably 100 to 200 degrees C. (373.15 K to 473.15 K) with an air volume of 3 to 50 l/(min·hole) or preferably 5 to 20 l/(min·hole). When fluid, mainly composed of gas, is blown based on the above conditions for example, such a fiber assembly is preferred as a fiber assembly of the present invention in which constituting fibers can have a different position or direction. By preparing the fiber assembly based on fiber and manufacture conditions as described above, the nonwoven fabric shown in FIGS. 1 and 2 for example can be formed. The groove portion 1 or the convex portion 2 can have a size or a basis weight of web in the following range. The groove portion 1 may have a thickness in the range of 0.05 to 10 mm or preferably 0.1 to 5 mm, a width of 0.1 to 30 mm or preferably 0.5 to 5 mm, and a basis weight of web of 2 to 900 g/m$^2$ or preferably 10 to 90 g/m$^2$. The convex portion 2 may have a thickness of 0.1 to 15 mm or preferably 0.5 to 10 mm, a width of 0.5 to 30 mm or preferably 1.0 to 10 mm, and a basis weight of web of 5 to 1000 g/m$^2$ or preferably 10 to 100 g/m$^2$. The groove portion 1 includes the open areas 3 with a predetermined interval and the open area 3 and the open area 3 have therebetween the joining portion 4. The open area 3 and the joining portion 4 may have a size and a basis weight of web within the following range. The joining portion 4 may have a thickness equal to or less than that of the convex portion 2, preferably 20 to 100%, or more preferably in the range of 40 to 70%, a width and a length in the range of 4 to 30 mm or preferably 5 to 10 mm, and a basis weight of web of 5 to 200 g/m$^2$ or preferably 10 to 100 g/m$^2$. The open area 3 may have a width and a length of 4 to 30 mm or preferably 5 to 10 mm. Although nonwoven fabric can be prepared by values within the above range, the invention is not limited to this range.

5.2.2. Air Permeable Supporting Member

The air permeable supporting member 200 exemplarily be a supporting member in which a face supporting the fiber web 100 has a substantially flat surface or a substantially curved surface and a surface in the substantially flat surface or the substantially curved surface is substantially flat. The substantially flat surface or substantially curved surface may exemplarily include, for example, a plate-like shape or a circular cylinder-like shape. The substantially flat shape may indicate, for example, a surface in the supporting member on which the fiber web 100 is placed has concavities and convexities for example. Specifically, the supporting member may exemplarily be the one which a mesh in the mesh supporting member 210 does not include concavities and convexities for example.

This air permeable supporting member 200 may exemplarily be, for example, a plate-like supporting member or a circular cylinder-like supporting member. Specifically, the above-described supporting member 240 or supporting member 275 may exemplarily be used.

The air permeable supporting member 200 can be detachably placed in the nonwoven fabric manufacture apparatus 90. Thus, the air permeable supporting member 200 depending on a desired nonwoven fabric can be appropriately placed. In other words, in the nonwoven fabric manufacture apparatus 90, the air permeable supporting member 200 can be exchanged with another air permeable supporting member selected from among a plurality of different air permeable supporting members.

The following section will describe a mesh part of the supporting member 240 shown in FIG. 3 and the supporting member 275 shown in FIG. 5. This air permeable mesh part may exemplarily be, for example, a air permeable net obtained by using thread by resin (e.g., polyester, polyphenylene sulfide, nylon, conductive monofilament) or thread by metal (e.g., stainless, copper, aluminum) and plain weave, diagonal weave, sateen weave, double cloth, or spiral intermeshed for example.

The air permeable net has an air permeability that can be partially changed, for example, by partially changing an intermeshing method, the thickness of a thread, or the shape of a thread. Specifically, this air permeable net may exemplarily be a spiral-intermeshed air permeable mesh made by polyester, or a spiral intermeshed air permeable mesh made by stainless by a flat thread and a circular thread.

Alternatively, a plate-like supporting member can be used. For example, a sleeve made of metal (e.g., stainless, copper, aluminum) may be exemplarily used. A sleeve may exemplarily be the one obtained by partially cutting the above metal plate by a predetermined pattern. Where the metal has been cut away functions as a pervious section and where the metal remains functions as an impervious section. As described above, an impervious section preferably has a smooth surface in order to improve the slipping property of the surface.

A sleeve may exemplarily be, for example, a stainless sleeve having a thickness of 0.3 mm obtained by rounding the respective corners of a rectangular metal plate extending in the lateral direction having a length of 3 mm and a width of 40 mm to cut metals to provide hole sections arranged with an interval of 2 mm in the line flow direction (moving direction) and an interval of 3 mm in the width direction to provide a lattice-like pattern.

Alternatively, a sleeve in which hole sections are arranged in a staggered manner also may be exemplarily used. For example, a stainless sleeve having a thickness of 0.3 mm may be exemplarily used in which circular hole sections having a diameter 4 mm obtained by cutting off metal are arranged in the line flow direction (moving direction) with a pitch of 12 mm and a pitch of 6 mm in the width direction to draw a staggered pattern. As described above, a pattern to be cut off (hole sections to be formed) or an arrangement can be appropriately determined.

Furthermore, the air permeable supporting member 200 including a predetermined undulating shape can be exemplarily used. For example, a air permeable supporting member exemplarily used that has parts that are not directly blown with fluid mainly composed of gas are alternately provided to draw an undulating pattern in the line flow direction (moving direction) (e.g., wave-like pattern). By using the air permeable supporting member 200 having the shape as described above, such nonwoven fabric can be obtained for example in which predetermined open areas are formed and projections are alternately provided in the entire air permeable supporting member 200 (e.g., wave-like pattern).

5.2.3. Blowing Means

By providing the blowing section 910 to be able to change the direction of fluid, mainly composed of gas, an interval between concave sections (groove portions) of the resultant concavities and convexities or the height of the convex portion can be appropriately adjusted for example. By providing the blowing section 910 to be able to automatically change the direction of the fluid for example, groove portions or the like can be appropriately adjusted to provide a meander pattern (wave-like pattern, zigzag pattern) or another pattern. By adjusting a blowing amount of a blowing time of fluid, mainly composed of gas, the shape or pattern of the groove portions or open areas can be appropriately adjusted. Fluid, mainly composed of gas, may be blown to the fiber web 100 in a vertical direction, with a predetermined angle inclined to the line flow direction in the moving direction F of the fiber web 100, or with a predetermined angle opposite to the line flow direction.

5.2.4. Heating Means

In the nonwoven fabric 180 including predetermined open areas, the fiber 101 can be adhered by, for example, the needle punch method, the span lace method, or the solvent welding method or can be thermal-adhered by the point bond method or the air through method. However, in order to maintain the shape of a predetermined open area, the air through method is preferred. For example, a thermal processing by the air through method by the heater section 950 is preferred.

5.2.5. Others

The nonwoven fabric 115 manufactured by being heated by the heater section 950 is moved by the conveyer 930 and the subsequent conveyer 940 in the predetermined direction F to a step for cutting or winding the nonwoven fabric 115 to have a predetermined shape for example. The conveyer 940 also may include the belt section 949, the rotation section 941 for example as in the conveyer 930.

While preferred embodiments of the present invention have been described and illustrated above, it is to be understood that they are exemplary of the invention and are not to be considered to be limiting. Additions, omissions, substitutions, and other modifications can be made thereto without departing from the spirit or scope of the present invention. Accordingly, the invention is not to be considered to be limited by the foregoing description and is only limited by the scope of the appended claims.

What is claimed is:

1. A nonwoven fabric, comprising:
   a plurality of groove portions recessed on a first face of the nonwoven fabric in a thickness direction, wherein the average basis weight of the groove portions is less than the average basis weight of the entire of the entire nonwoven fabric;
   wherein the groove portions include:
      a plurality of open areas arranged in a longitudinal direction and passing through the entire nonwoven fabric in the thickness direction; and
      a plurality of joining portions each of which is provided between a predetermined open area among the plurality of open areas and another open area adjacent to the predetermined open area in the longitudinal direction, wherein each of the joining portions include:
         fibers with a greater content oriented in a width direction compared to that oriented in a longitudinal direction,
         a fiber density greater than that of the plurality of peripheral regions that are formed in the longitudinal direction along the plurality of open areas and the plurality of joining portions, and
         a ratio of a length in the longitudinal direction to a length in the width direction no greater than 0.7; and
   a plurality of convex portions that are adjacent to and along the plurality of groove portions and that protrude from the first face of the nonwoven fabric in the thickness direction each of said plurality of convex portions has a greater width than the average basis weight of the plurality of groove portions.

2. The nonwoven fabric according to claim 1, wherein fibers around a periphery edge of each of the open areas are oriented along the periphery edge of the open area.

3. The nonwoven fabric according to claim 1, wherein each of the open areas has a substantially circular shape or a substantially oval shape.

4. The nonwoven fabric according to claim 1, wherein each of the open areas has a length in the longitudinal direction and a length in the width direction of 5 to 10 mm.

5. The nonwoven fabric according to claim 1, wherein each of the open areas has a length in the width direction of 4 to 30 mm.

6. The nonwoven fabric according to claim 1, wherein each of the groove portions has a height in the thickness direction of the nonwoven fabric that is no greater than 90% of the height of each of the convex portions.

7. The nonwoven fabric according to claim 1, wherein a predetermined convex portion among the plurality of convex portions has a different height from an adjacent convex portion, wherein the predetermined convex portion and the adjacent convex portion are arranged to sandwich therebetween a predetermined groove portion among the plurality of groove portions.

8. The nonwoven fabric according to claim 1, wherein each of the convex portions has an apex portion having a substantially flat shape.

9. The nonwoven fabric according to claim 1, wherein a second face of the nonwoven fabric opposite to the first face comprises a plurality of protruding regions protruding in an opposite direction to a direction in which the convex portions protrude.

10. The nonwoven fabric according to claim 1, wherein the nonwoven fabric has an undulating surface substantially orthogonal to a direction in which the plurality of groove portions and the plurality of convex portions extend.

11. The nonwoven fabric according to claim 1, wherein a second face of the nonwoven fabric opposite to the first face is substantially flat.

12. The nonwoven fabric according to claim 1, wherein side sections of each of the plurality of convex portions comprise a higher content of fibers oriented in the longitudinal direction compared to that oriented in the width direction.

13. The nonwoven fabric according to claim 1, wherein a percent open area measured from the first face is greater than that measured from a second face of the nonwoven fabric which is opposite to the first face.

14. The nonwoven fabric according to claim 1, wherein each of the joining portions has a fiber density of no less than 0.05 g/cm$^3$.

15. The nonwoven fabric according to claim 1, wherein fibers constituting the nonwoven fabric include water-repellent fibers.

16. The nonwoven fabric according to claim 1, wherein the peripheral region formed in the longitudinal direction along each of the open areas has a fiber density that gradually increases in the longitudinal direction from a center of said peripheral region toward both ends of said open area.

* * * * *